United States Patent [19]
Dickson et al.

[11] Patent Number: 5,583,030
[45] Date of Patent: Dec. 10, 1996

[54] METHOD FOR OBTAINING ANTIFUNGAL AND HERBICIDAL COMPOUNDS THAT TARGET THE FIRST COMMITTED STEP IN SHINGOLIPID LONG-CHAIN BASE BIOSYNTHESIS

[75] Inventors: Robert C. Dickson; Robert L. Lester, both of Lexington, Ky.

[73] Assignee: The University of Kentucky Research Foundation, Lexington, Ky.

[21] Appl. No.: 365,981

[22] Filed: Dec. 28, 1994

Related U.S. Application Data

[63] Continuation of Ser. No. 906,899, Jun. 30, 1992, abandoned.

[51] Int. Cl.$^6$ .............................. C12N 1/15; C12N 1/19; C12N 1/21; C12N 5/10; C12N 15/54; C12N 15/63
[52] U.S. Cl. ..................................... 435/240.1; 435/252.3; 435/254.11; 435/320.1; 435/172.3; 435/193; 536/23.2
[58] Field of Search .............................. 536/23.2, 23.74; 435/240.1, 252.3, 254.11, 256, 320.1, 193

[56] References Cited

PUBLICATIONS

Nagiec et al., (1994) Proc. Nat. Acad. Sci., USA 91:.
Pinto et al., (1986) Federation Proceedings 45: 1826.
Wells et al., (1983) J. Biological Chemistry 258: 10200–10203.

*Primary Examiner*—Robert A. Wax
*Assistant Examiner*—Gabriele E. Bugaisky
*Attorney, Agent, or Firm*—Lowe, Price, LeBlanc & Becker

[57] ABSTRACT

The invention provides the LCB1 and LCB2 genes of the yeast *Saccharomyces cerevisiae* that encode subunits of the enzyme serine palmitoyltransferase (SPT), the first enzyme leading to synthesis of the long-base component of the sphingolipids. The present specification describes the isolation of the LCB1 and LCB2 genes. The invention further relates to methods of using these genes to either inhibit SPT activity or to inhibit synthesis of the enzyme. Furthermore, the invention relates to methods for constructing strains of *S. cerevisiae* or other organisms that can be used to select and to test for compounds that either inhibit SPT activity or to inhibit synthesis of the enzyme.

12 Claims, 11 Drawing Sheets

FIGURE 2A

```
CGC GTA TTT TTT TTT TTT TGA GGC GCC ATG ATT TCT TAC ACG GTT TCT TTT TTT TTT
              -319                    -304                    -289
CCT TCT TTC CTT CTT GCT TCT CTG CTA ACA AAT TTT TCA CTC ATT CTT TTT TAT AGG
-274                    -259                    -244                    -229
GGC ATA TTG CTG CGG TTA ACT GTA GTG AAC GAA AGT AAG ATT GAG AAA ATA TAG TAC
    -214                    -199                    -184                    -169
TTA AGA AAA AGA AAA GGA AAA ATA AAA AAA ATT CTT TTC AAC ATC ATC GAG TAG CAC
        -154                    -139                    -124                    -109
AGT ATA AGA GCG CTC TAA CCT TCT GCC TGG CCT CCA ATA TAC ACA TTT TGC TCG TGT
            -94                     -79                     -64                     -49
                                    * *                                      M   A   H
AGG GTT ATT TAT CCT TTT TTC TTC CTT CCC ACC CAA AAA AAA AAA GCA ATG GCA CAC
                -34                     -19                      -4  +1
 I   P   E   V   L   P   K   S   I   P   I   P   A   F   I   V   T   T   S
ATC CCA GAG GTT TTA CCC AAA TCA ATA CCG ATT CCG GCA TTT ATT GTT ACC ACC TCA
 12                  27                      42                      57
 S   Y   L   W   Y   Y   F   N   L   V   L   T   Q   I   P   G   Q   F
TCG TAC CTA TGG TAC TAC TTC AAT CTG GTG TTG ACT CAA ATC CCG GGA GGC CAA TTC
     72                      87                     102                     117
 I   V   S   Y   I   K   K   S   H   H   D   D   P   Y   R   T   T   V   E
ATC GTT TCG TAC ATC AAG AAA TCG CAT CAT GAC GAT CCA TAC AGG ACC ACG GTT GAG
        132                     147                     162                     177
 I   G   L   I   L   Y   G   I   I   Y   Y   L   S   K   P   Q   Q   K   K
ATA GGG CTT ATT TTA TAC GGG ATC ATC TAT TAC TTG TCC AAG CCA CAA CAG AAA AAG
            192                     207                     222                     237
 S   L   Q   A   Q   K   P   N   L   S   P   Q   E   I   D   A   L   I   E
AGT CTT CAA GCA CAG AAG CCC AAC CTA TCG CCC CAG GAG ATT GAC GCG CTA ATT GAG
                252                     267                     282
 D   W   E   P   E   P   L   V   D   P   S   A   T   D   E   Q   S   W   R
GAC TGG GAG CCC GAG CCT CTA GTC GAC CCT TCT GCC ACC GAT GAG CAA TCG TGG AGG
297                     312                     327                     342
 V   A   K   T   P   V   T   M   E   M   P   I   Q   N   H   I   T   I   T
GTG GCC AAA ACA CCC GTC ACC ATG GAA ATG CCC ATT CAG AAC CAT ATT ACT ATC ACC
    357                     372                     387                     402
 R   N   N   L   Q   E   K   Y   T   N   V   F   N   L   A   S   N   N   F
AGA AAC AAC CTG CAG GAG AAG TAT ACC AAT GTT TTC AAT TTG GCC TCG AAC AAC TTT
        417                     432                     447                     462
 L   Q   L   S   A   T   E   P   V   K   E   V   V   K   T   T   I   K   N
TTG CAA TTG TCC GCT ACG GAG CCC GTG AAA GAA GTG GTC AAG ACC ACT ATC AAG AAT
            477                     492                     507                     522
 Y   G   V   G   A   C   G   P   A   G   F   Y   G   N   Q   D   V   H   Y
TAC GGT GTG GGC GCC TGT GGT CCC GCC GGG TTC TAC GGT AAC CAG GAC GTT CAT TAC
                537                     552                     567
 T   L   E   Y   D   L   A   Q   F   F   G   T   Q   G   S   V   L   Y   G
ACG TTG GAA TAT GAT TTA GCA CAG TTC TTT GGC ACC CAA GGT TCC GTT CTG TAC GGG
582                     597                     612                     627
 Q   D   F   C   A   A   P   S   V   L   P   A   F   T   K   R   G   D   V
CAA GAC TTT TGT GCC GCA CCC TCT GTT CTG CCT GCT TTC ACA AAG CGT GGT GAT GTT
    642                     657                     672                     687
 I   V   A   D   D   Q   V   S   L   P   V   Q   N   A   L   Q   L   S   R
ATC GTG GCA GAC GAC CAG GTG TCA TTA CCA GTG CAA AAT GCT CTG CAA CTA AGC AGA
        702                     717                     732                     747
 S   T   V   Y   Y   F   N   H   N   D   M   N   S   L   E   C   L   L   N
TCC ACA GTC TAC TAC TTC AAC CAC AAC GAT ATG AAT TCG CTA GAA TGT TTA TTA AAC
            762                     777                     792                     807
 E   L   T   E   Q   E   K   L   E   K   L   P   A   I   P   R   K   F   I
GAG TTG ACC GAA CAG GAG AAA CTT GAG AAA CTG CCC GCC ATT CCA AGA AAA TTT ATC
                822                     837                     852
 V   T   E   G   I   F   H   N   S   G   D   L   A   P   L   P   E   L   T
GTC ACT GAG GGT ATT TTC CAC AAC TCG GGC GAT TTA GCT CCG TTG CCT GAG TTG ACT
867                     882                     897                     912
```

FIGURE 2B

```
  K   L   K   N   K   Y   K   F   R   L   F   V   D   E   T   F   S   I   G
AAG CTG AAG AAC AAG TAC AAG TTC AGA CTA TTT GTT GAC GAA ACC TTC TCC ATT GGT
    927                 942                 957                 972
  V   L   G   A   T   G   R   G   L   S   E   H   F   N   M   D   R   A   T
GTT CTT GGC GCT ACG GGC CGT GGG TTG TCA GAG CAC TTC AAC ATG GAT CGC GCA ACT
        987                1002                1017                1032
  A   I   D   I   T   V   G   S   M   A   T   A   L   G   S   T   G   G   F
GCC ATT GAC ATT ACC GTT GGG TCC ATG GCC ACC GCG TTG GGG TCC ACC GGT GGT TTT
            1047                1062                1077                1092
  V   L   G   D   S   V   M   C   L   H   Q   R   I   G   S   N   A   Y   C
GTC CTG GGT GAC AGT GTT ATG TGT TTG CAC CAG CGT ATT GGT TCC AAT GCA TAT TGT
                1107                1122                1137
  F   S   A   C   L   P   A   Y   T   V   T   S   V   S   K   V   L   K   L
TTT TCT GCC TGT TTG CCG GCT TAC ACC GTC ACA TCC GTC TCC AAA GTC TTG AAA TTG
1152                1167                1182                1197
  M   D   S   N   N   D   A   V   Q   T   L   Q   K   L   S   K   S   L   H
ATG GAC TCC AAC AAC GAC GCC GTC CAG ACG CTG CAA AAA CTA TCC AAA TCT TTG CAT
    1212                1227                1242                1257
  D   S   F   A   S   D   D   S   L   R   S   Y   V   I   V   T   S   S   P
GAT TCC TTT GCA TCT GAC GAC TCC TTG CGT TCA TAC GTA ATC GTC ACG TCC TCT CCA
        1272                1287                1302                1317
  V   S   P   V   L   H   L   Q   L   T   P   A   Y   R   S   R   K   F   G
GTG TCT CCT GTC CTA CAT CTG CAA CTG ACT CCC GCA TAT AGG TCT CGC AAG TTC GGA
            1332                1347                1362                1377
  Y   T   C   E   Q   L   F   E   T   M   S   A   L   Q   K   K   S   Q   T
TAC ACC TGC GAA CAG CTA TTC GAA ACC ATG TCA GCT TTG CAA AAG AAG TCC CAG ACA
                1392                1407                1422
  N   K   F   I   E   P   Y   E   E   E   K   F   L   Q   S   I   V   D
AAC AAA TTC ATT GAG CCA TAC GAA GAG GAG GAA AAA TTT CTG CAG TCC ATA GTA GAT
1437                1452                1467                1482
  H   A   L   I   N   Y   N   V   L   I   T   R   N   T   I   V   L   K   Q
CAT GCT CTT ATT AAC TAC AAC GTT CTC ATC ACA AGA AAC ACT ATT GTT TTA AAA CAG
    1497                1512                1527                1542
  E   T   L   P   I   V   P   S   L   K   I   C   C   N   A   A   M   S   P
GAG ACG CTA CCA ATT GTC CCT AGC TTG AAA ATC TGC TGT AAC GCC GCC ATG TCC CCA
        1557                1572                1587                1602
  E   E   L   K   N   A   C   E   S   V   K   Q   S   I   L   A   C   C   Q
GAG GAA CTC AAA AAT GCT TGC GAA AGT GTC AAG CAG TCC ATC CTT GCC TGT TGC CAA
            1617                1632                1647                1662
  E   S   N   K
GAA TCT AAT AAA TAA AAA TAG AAA GCC AGT ATA TGC ACA CGC ACA TAT ATA TAT AAA
                1677                1692                1707
TAT TTA TAC AAT AAT ACA AAT AAT CGT AAC ATC ATC TCT GTC AAA TTG ACG TGG TGC
1722                1737                1752                1767
ACG GCG CCC AGA GAA TGC GCT AAA AAT TTT CGG ATC CGA AAT TTT CTT TCC TTT TAC
    1782                1797                1812                1827
CAT CGA GGC AAA GCA ACC TGT ATT ATT TAT TTG TTT ATT TAT TAA TAG AAA AGA AAG
        1862                1857                1872                1887
GAG TAC TTT CGT GGT ACG CTT TCT TGA GCA TTT TCG GTT TCA CTA GGC AGA GAA CTA
            1922                1917                1932                1967
ACA CAA GAG ACA CAG CAA ACA TCA AAC AAG GTT AAA ACA GCA CAC CAA GGC AAT ATG
                1982                1977                1992
ATG CAT TTT AGA AAG AAA TCC AGT ATC AGT AAC ACG AGT GAT CAT GAC GGA GCG AAC
2007                2022                2037                2052
CGT GCC TCA GAT GTC AAG ATT TCT GAA GAT GAC AAG GCA AGA TTG AAG ATG CGT ACT
    2067                2082                2097                2112
GCT TCC GTT GCT GAT CCT A
    2127
```

```
                          10        20        30        40        50
EKBL#₈₁                                            FICGTQDSHKELEQKLA  #₉₇
                                                   ...::: : .:: .::
LCB1#₁₅₀  LASNNFLQLFATEPVKEVVKTTIKNYGVGACGPAGFYGNQDVHYTLEYDLA  #₂₀₀
          ::..:  .       .: .....:.::.:.:: :.  .. :. . : .::..::
ALSM#₁₉₃  WCSNDYLGISRHPRVLQAIEETLKNHGAGAGGTRNISGTSKFHVELEQELA  #₂₄₃
          ::..:.:     :  .....::..:: :: :. .. :..   .:: .::
ALSC#₂₄₃  WCSNDYLGMSRHPRVCGAVMDTKLQHGAGAGGTRNISGTSKFHVDLEKELA  #₂₉₃
          ::..:.:     :  .....::..:: :: :. .. :...    .:: .::
ALSY#₁₁₈  WCSNKYLALSKHPEVLDAMHKTIDKYGCGAGGTRNIAGHNIPTLNLEAELA  #₁₆₈

10        20        30        40        50
EKBL#₉₈   AFLGMEDAILYSSCFDANGGLFETLLG--AEDALISDALNHASIIDGVRLC  #₁₄₆
          .:.: ....::. : :. ... ..      :.:...:.  .  .....:
LCB1#₂₀₁  QFFGTQGSVLYGQDFCAAPSVLPAFTK--RGDVIVADDQVSLPVQNALQLS  #₂₄₉
          ..  .......:..  : :. :.: ...:  .: : .::     .. .... :
ALSM#₂₄₄  ELHQKDSALLFSSCFVANDSTLFTLAKLLPGCEIYSDAGNHASMIQGIRNS  #₂₉₄
          .. :........ : :. .:.: ...:  .:  : .::     .. .... :
ALSC#₂₉₄  DLHGKDAALLFSSCFVANDSTLFTLAKMLPGCEIYSDSGNHASMIQGIRNS  #₃₄₄
          .  ..:...... . :. .::. .. :. :.:. .:::         ..  ... .
ALSY#₁₆₉  TLHKKEGALVFSSCYVANDAVLSLLGQKMKDLVIFSDELNHASMIVGIKHA  #₂₁₉

10        20        30        40        50
EBIO#₁₇₀                                    QMVVTEGVFSMDGDS  #₁₈₄
                                            ...:::::.:  .::
EKBL#₁₄₇  KAKRYRYANNDMQELEARLKEARERG-----ARH-VLIATDGLFSMDGVI  #₁₉₀
          ... :  ...:::...::   : : :          :   .:.:.:.: :  .
LCB1#₂₅₀  RSTVYYFNHNDMNSLECLLNELTEQEKLEKLPAIPRKFIVTEGIFHNSGDL  #₃₀₀
          .. .  . :.:::. :...::     ::  ... ... :..    .:..
ALSM#₂₉₅  GAAKFVFRHNDPGHLKKLL--------EKSDPKTPKIVAFETVHSMDGAI  #₃₃₆
          : . . :..:::..: .::         .: . ...:... :..    .:..
ALSC#₃₄₅  RVPKHIFRHNDVNHLRELL--------KKSDPSTPKIVAFETVHSMDGAV  #₃₈₆
          .. :  :.:::::..:: ::       .. : .:.:. :....  .:..
ALSY#₂₂₀  NVKKHIFKHNDLNELEQLL--------QSYPKSVPKLIAFESVYSMAGSV  #₂₆₁
```

FIGURE 3B

```
                  10        20        30        40        50
EBIO#₁₈₅  APLAEIQQVTQQHNGWLMVDDAHGTGVIGEQGRG                      #₂₁₈
          ::::.:  ........  .:.::..  ..:.:.  :::
EKBL#₁₉₁  ANLKGVCDLADKY                                           #₂₀₃
          : : .. .: .::
LCB1#₃₀₁  APLPELTKLKNKYKFRLFVDETFSIGVLGATGRGL-------------        #₃₃₅
          :: :: .. ..: ::::. ...:. :: : :.
ALSM#₃₃₇  CPLEELCDVAHQYGALTFVDEVHAVGLYGARGAGI-------------        #₃₇₁
          :: :: .. ... ::::. ...:. :: : :.
ALSC#₃₈₇  CPLEELCDVAHEHGAITFVDEVHAVGLYGARGGGI-------------        #₄₂₁
          : .. .: .:: :..::. ...:. :. : :.
ALSY#₂₆₂  ADIEKICDLADKYGALTFLDEVHAVGLYGPHGAGVAEHCDFESHRASGIAT     #₃₁₂

10        20        30        40        50
LCB1#₃₃₆  ------SEH--FNMDRATAIDITVGSMATALGSTGGFVLGDSVNCLHQRIG      #₃₇₈
               .:.    .    .:::. :.....:.:..::..  ...      :
ALSM#₃₇₂  ------GER----DGIMHKLDIISGTLGKAFGCVGGYIASTRDLVDMVRSY     #₄₁₂
               ...    .    .:::. :.....:.....::.. ...:.
ALSC#₄₂₂  ------GDR----DGVMHKMDIISGTLGKAFACVGGYISSTSALIDTVRSY     #₄₆₂
               .:.    .    .:::. .:.:.... :::.::.  ..       :
ALSY#₃₁₃  PKTNDKGGA----KTVMDRVDMITGTLGKSFGSVGGYGAASRKLIDWFRSF      #₃₆₃

LCB1#₃₇₉  SNAYCFSACLPAYTVTSVSKVLKLMDSNNDAV                        #₄₁₀
          .... :...::.  .... :  ...:.... .
ALSM#₄₁₃  AAGFIFTTSLPPMMLSGALESVRLLKGEEGQA                        #₄₄₄
          .... :...::.  .... . ..  ..:....:
ALSC#₄₆₃  AAGFIFTTSLPPMLLAGALESVRTLKSAEGQV                        #₄₉₄
          . .. :... ::. ...... ...       :
ALSY#₃₆₄  APGFIFTTTLPPSVMAGATAAIRYQRCHIDLR                        #₃₉₁
```

FIGURE 4
SERINE PALMITOYLTRANSFERASE:
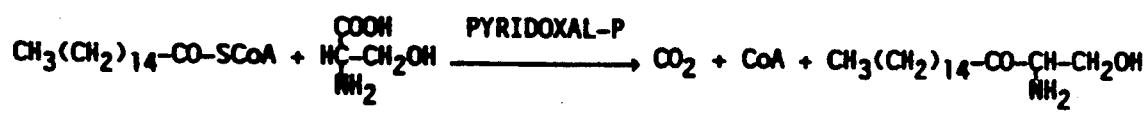
5-AMINOLEVULINIC ACID SYNTHASE:
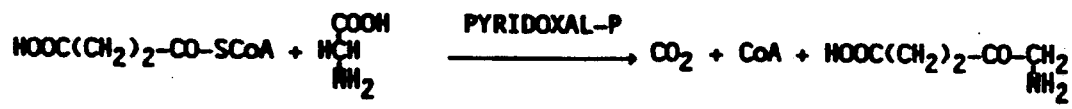
2-AMINO-3-KETOBUTYRATE LIGASE:
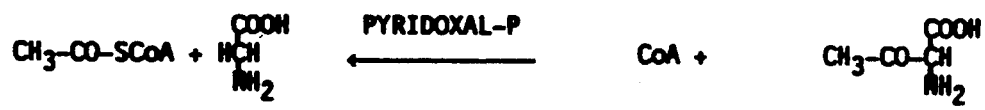

FIGURE 5
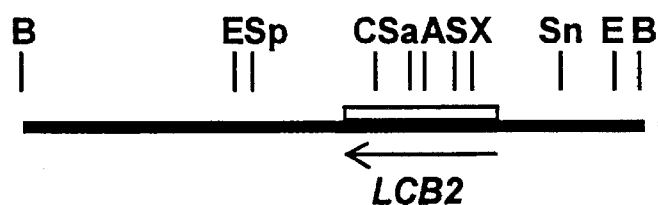
A
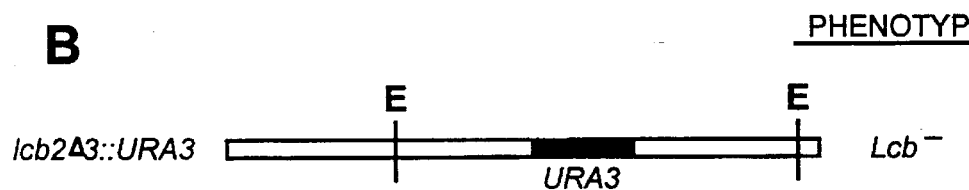
| NAME | | COMPLEMENT lcb2 |
|---|---|---|
| B7 | | + |
| B7ΔS | | − |
| 2.3 | | − |
| LCB2-R | | + |
B
PHENOTYPE
lcb2Δ3::URA3     Lcb⁻
C
pRSLCB2-2
1 kb

FIGURE 6A

```
-883 GCAAATATTGATTCTCGATGAGGCATTTTCTGGAATGGAGGTAGAACCTATGATGCGTTG
-823 TCATGAATTTTTAGAGGAGTGGCCTGGAACAGTCCTTGTAGTGGCACACGTTGCCGAAGA
-763 GACACCAAAATGTGCCCATTACTTAAGGCTCATATCTCCTGGAGAGTATGAAATAGGCGA
-703 TATGGAAAATTAAAGTTTTCTGTTGTGTGGCAGCAAGAGACAGAACCTCGATAATTTGAC
-643 ATACGTATATAATAGTACATGTACATAAAAACGTACGCAAATATCGTATATCTGTTATAC
-583 TACAAAACAATTACTTCTATATCATAGCCAGTTAGCGGGAACGACTTCAGCTAAATGGAC
-523 TATCCATGCTTTAGGCAGAGGCGAAGCGCGGTGATTGGGTGTAACATCATCTCCTTTTCT
-463 CTACGACAAATTCCCAAAAAAAAAATTTATGCTATGTTAATACCTGCACAATTCAACCGT
-403 GCTGAAACGTAAAATTAAGGTGATTATACGGATAGTATACGATATTATCAATCTCATAAG
-343 AAAAATCTCTTTTGAATTTAACGGAGGGATTATTCATTAGAAAGCGTTCTTACCATTCAC
-283 TAGGAGCGAATCCGTGGAAGGTGTTTTAACGTTGCCACGAAAAACAGCTCTACATCGAAA
-223 TAAAAGACAACAATCAGTGCCCGTAAGTTTCATTACTATTTTCTATTATTATCTGCAACT
-163 TTTTATTAGTTAGGTTTTTTTTGTTTGTTTGTTTGTTTTCAATTGATTAATTTACAAGAC
-103 AAAGAACCTTATATTTCGTGTTTTTCATTCTAAAGGAAAAAAAGCATAAAGAAGATTCCA
 -43 CACACTTTATTGTGATAGTTTTCAAAGTAAAAAGTAATAGATTATGAGTACTCCTGCAAA
                                                M  S  T  P  A  N    6

18 CTATACCCGTGTGCCCCTGTGCGAACCAGAGGAGCTGCCAGACGACATACAAAAGAAAA
      Y  T  R  V  P  L  C  E  P  E  E  L  P  D  D  I  Q  K  E  N   26

78 TGAATATGGTACACTAGATTCTCCGGGGCATTTGTATCAAGTCAAGTCACGTCATGGGAA
      E  Y  G  T  L  D  S  P  G  H  L  Y  Q  V  K  S  R  H  G  K   46

138 GCCACTACCTGAGCCCGTTGTCGACACCCCTCCTTATTACATTTCTTTGTTAACATATCT
      P  L  P  E  P  V  V  D  T  P  P  Y  Y  I  S  L  L  T  Y  L   66

198 AAATTATTTGATTCTGATTATATTAGGTCATGTTCACGACTTCTTAGGTATGACCTTCCA
      N  Y  L  I  L  I  I  L  G  H  V  H  D  F  L  G  M  T  F  Q   86

258 AAAAAACAAACATCTGGATCTTTTAGAGCATGATGGGTTAGCACCTTGGTTTTCAAATTT
      K  N  K  H  L  D  L  L  E  H  D  G  L  A  P  W  F  S  N  F  106

318 CGAGAGTTTTTATGTCAGGAGAATTAAAATGAGAATTGATGATTGCTTTTCTAGACCAAC
      E  S  F  Y  V  R  R  I  K  M  R  I  D  D  C  F  S  R  P  T  126

378 TACTGGTGTTCCTGGTAGATTTATTCGTTGTATTGATAGAATTTCTCATAATATAAATGA
      T  G  V  P  G  R  F  I  R  C  I  D  R  I  S  H  N  I  N  E  146

438 GTATTTTACCTACTCAGGCGCAGTGTATCCATGCATGAACTTATCATCATATAACTATTT
      Y  F  T  Y  S  G  A  V  Y  P  C  M  N  L  S  S  Y  N  Y  L  166

498 AGGCTTCGCACAAAGTAAGGGTCAATGTACCGATGCCGCCTTGGAATCTGTCGATAAATA
      G  F  A  Q  S  K  G  Q  C  T  D  A  A  L  E  S  V  D  K  Y  186

558 TTCTATTCAATCTGGTGGTCCAAGAGCTCAAATCGGTACCACAGATTTGCACATTAAAGC
      S  I  Q  S  G  G  P  R  A  Q  I  G  T  T  D  L  H  I  K  A  206

618 AGAGAAATTAGTTGCTAGATTTATCGGTAAGGAGGATGCCCTCGTTTTTTCGATGGGTTA
      E  K  L  V  A  R  F  I  G  K  E  D  A  L  V  F  S  M  G  Y  226

678 TGGTACAAATGCAAACTTGTTCAACGCTTTCCTCGATAAAAAGTGTTTAGTTATCTCTGA
      G  T  N  A  N  L  F  N  A  F  L  D  K  K  C  L  V  I  S  D  246

738 CGAATTGAACCACACCTCTATTAGAACAGGTGTTAGGCTTTCTGGTGCTGCTGTGCGAAC
      E  L  N  H  T  S  I  R  T  G  V  R  L  S  G  A  A  V  R  T  266

798 TTTCAAGCATGGTGATATGGTGGGTTTAGAAAAGCTTATCAGAGAACAGATAGTACTTGG
      F  K  H  G  D  M  V  G  L  E  K  L  I  R  E  Q  I  V  L  G  286

858 TCAACCAAAAACAAATCGTCCATGGAAGAAAATTTTAATTTGCGCAGAAGGGTTGTTTTC
      Q  P  K  T  N  R  P  W  K  K  I  L  I  C  A  E  G  L  F  S  306
```

FIGURE 6B

```
 918 CATGGAAGGTACTTTGTGTAACTTGCCAAAATTGGTTGAATTGAAGAAGAAATATAAATG
      M  E  G  T  L  C  N  L  P  K  L  V  E  L  K  K  K  Y  K  C   326

978 TTACTTGTTTATCGATGAAGCCCATTCTATAGGCGCTATGGGCCCAACTGGTCGCGGTGT
      Y  L  F  I  D  E  A  H  S  I  G  A  M  G  P  T  G  R  G  V   346

1038 TTGTGAAATATTTGGCGTTGATCCCAAGGACGTCGACATTCTAATGGGTACTTTCACTAA
      C  E  I  F  G  V  D  P  K  D  V  D  I  L  M  G  T  F  T  K   366

1098 GTCGTTTGGTGCTGCTGGTGGTTACATTGCTGCTGATCAATGGATTATCGATAGACTGAG
      S  F  G  A  A  G  G  Y  I  A  A  D  Q  W  I  I  D  R  L  R   386

1158 GTTGGATTTAACCACTGTGAGTTATAGTGAGTCAATGCCGGCTCCTGTTTTAGCTCAAAC
      L  D  L  T  T  V  S  Y  S  E  S  M  P  A  P  V  L  A  Q  T   406

1218 TATTTCCTCATTACAAACCATTAGTGGTGAAATATGTCCCGGACAAGGTACTGAAAGATT
      I  S  S  L  Q  T  I  S  G  E  I  C  P  G  Q  G  T  E  R  L   426

1278 GCAACGTATAGCCTTTAATTCCCGTTATCTACGTTTAGCTTTGCAAAGGTTAGGATTTAT
      Q  R  I  A  F  N  S  R  Y  L  R  L  A  L  Q  R  L  G  F  I   446

1338 TGTCTACGGTGTGGCTGACTCACCAGTTATTCCCTTACTACTGTATTGTCCCTCAAAGAT
      V  Y  G  V  A  D  S  P  V  I  P  L  L  L  Y  C  P  S  K  M   466

1398 GCCCGCATTTTCGAGAATGATGTTACAAAGACGGATTGCTGTTGTTGTTGTTGCTTATCC
      P  A  F  S  R  M  M  L  Q  R  R  I  A  V  V  V  V  A  Y  P   486

1458 TGCTACTCCGCTGATCGAATCAAGAGTAAGATTCTGTATGTCTGCATCTTTAACAAAGGA
      A  T  P  L  I  E  S  R  V  R  F  C  M  S  A  S  L  T  K  E   506

1518 AGATATCGATTATTTACTGCGTCATGTTAGTGAAGTTGGTGACAAATTGAATTTGAAATC
      D  I  D  Y  L  L  R  H  V  S  E  V  G  D  K  L  N  L  K  S   526

1578 AAATTCCGGCAAATCCAGTTACGACGGTAAACGTCAAAGATGGGACATCGAGGAAGTTAT
      N  S  G  K  S  S  Y  D  G  K  R  Q  R  W  D  I  E  E  V  I   546

1638 CAGGAGAACACCTGAAGATTGTAAGGACGACAAGTATTTTGTTAATTGAATTTTACCTAA
      R  R  T  P  E  D  C  K  D  D  K  Y  F  V  N                  561

1698 TTGCTAGTTAGGTGAAAAATTACAAAATTTCTGGAAGACGTTGGAAACACGCAACGTCTT
1758 TTTGACATAAACTTAAAACTGCCAAAAGTCAAACAAAAATTGCAAAAAAAGTAAAAAAAG
1818 TTACGAAAAAAAAAACATTTAAAAGAAAGAAGAAGTTAAAAGTGCACGCAATATGTTCCA
1878 GGATATGAAATGAAATACCTTTTGTTTCACCTTTTAAATAATTTAATGTTATATATACAA
1938 CTTTATCGTATCATATTCGCAATTACATTATACAAGAATGAGTTTTTTTTCGCGACAAAG
```

FIGURE 7A

```
              *         *     *  *        *            **    *  ,
LCB1          MAHIPE----VLPKSIPIPAFIVTTSSYLWYYFNLVLTQIPGGQFIVSYI         46
LCB2          MSTPANYTRVPLCEPEELPDDIQKENEY-------GTLDSPGHLYQV---         40
HEM1$YEAST    MQR-SIFAR--FGNSSAAVSTLNR-----------LSTTAAPHAKNGYA         35
              *         .  ...    ..                        ..

** *  *        *       * *  *     *          **
LCB1          KKSHHDDPYRTTVE------IGLILYG---IIYYLSKPQQKKSLQAQKPN        87
LCB2          -KSRHGKPLPEPVVDTPPYYISLLTYLNYLILIILGHVHDFLGMTFQKNK        89
HEM1$YEAST    TATGAGAAAATATASS------------------THAAAAAAAAANHST        66
              .  .. ...                                  .. .  .. .

*              *
LCB1          ----LSPQEIDALIEDWEPEPLVDPSATDEQSWRVAKTPVTMEMPI-QNH       132
LCB2          HLDLLEHDGLAPWFSNFESFYVRRIKMRIDDCF--SRPTTGVPGRF-IRC       136
HEM1$YEAST    QESGFDYEGLID--SELQ-------KKRLDKSYRYFNNINRLAKEFPLAH       107
              ..  ...        ...           ....         .

*    *  *  *    *   ** *  *                       *
LCB1          ITITRNNLQEKYT---NVF---NLASNNFLQLSATE-PVKEVVKTTIKNY       175
LCB2          IDRISHNINEYFTYSGAVYPCMNLSSYNYLGFAQSKGQCTDAALESVDKY       186
HEM1$YEAST    RQREADKVTVW---------C----SNDYLALSK-HPEVLDAMHKTIDKY       143
              ...                  *   *...*  ..   .   .....*

**      *  *  *    *    * * *               **
LCB1          GVGACGPAGFYGNQDVHYTLEYDLAQFFGTQGSVLYGQDFCAAPSVLPAF       225
LCB2          SIQSGGPRAQIGTTDLHIKAEKLVARFIGKEDALVFSMGYGTNANLFNAF       236
HEM1$YEAST    GCGAGGTRNIAGHNIPTLNLEAELATLHKKEGALVFSSCYVANDAVLSLL       193
              . .*..  .*       .  * .*.    .........  .

*       **   *  *   * **  ** *   *
LCB1          TKR-GDVIV-ADDQVSLPVQNALQLSRSTVYYFNHNDMNSLECLLNELTE       273
LCB2          LDK-KCLVI-SDELNHTSIRTGVRLSGAAVRTFKHGDMVGLEKLIREQIV       284
HEM1$YEAST    GQKMKDLVIFSDELNHASMIVGIKHANVKKHIFKHNDLNELEQLL-----       238
              ..   ... .*.    ..  ....        *.*.*. .** *.

* **   *  *     *      *   * **  *** ** **
LCB1          QEKLEKLPAIPRKFIVTEGIFHNSGDLAPLPELTKLKNKYKFRLFVDETF       323
LCB2          LGQPKTNRPWKKILICAEGLFSMEGTLCNLPKLVELKKKYKCYLFIDEAH       334
HEM1$YEAST    ----QSYPKSVPKLIAFESVYSMAGSVADIEKICDLADKYGALTFLDEVH       284
              ...         .*   *...   .*..  ...   .* .**    *.**.

***  * ****  *     *    *                          ** *
LCB1          SIGVLGATGRGLSEH--FNMDRATAI-----------------DITVGS        353
LCB2          SIGAMGPTGRGVCEI--FGVD-PKDV-----------------DILMGT        363
HEM1$YEAST    AVGLYGPHGAGVAEHCDFESHRASGIATPKTNDKGGAKTVMDRVDMITGT        334
              ..*  *. * *. *   *.. .    ....              *.   *.

*   **    *          *         *     **       *
LCB1          MATALGSTGGFVLGDSVMCLHQRIGSNAYCFSACLPAYTVTSVSKVLKLM       403
LCB2          FTKSFGAAGGYIAADQWIIDRLRLDLTTVSYSESMPAPVLAQTISSLQTI       413
HEM1$YEAST    LGKSFGSVGGYVAASRKLIDWFRSFAPGFIFTTTLPPSVMAGATAAIRYQ       384
              .....*...**..  .         *    . ....*. ....  . ..

*     *              *   **   ***  * *
LCB1          DSNNDAVQTLQKLSK-SLHDSFASDDSLRSYVIVTSSPVSPVLHLQLTPA       452
LCB2          SGEICPGQGTERLQRIAFNSRYLRLALQRLGFIVYGVADSPVIPLLL---       460
HEM1$YEAST    RCHIDLRTSQQK------HTMYVKKAFHELGIPVIPNP-SHIVPVLIGNA       427
              .    ...                     *    .*......

*   *                    *  **   *** * *
LCB1          YRSRKFG---------YTCEQLFETMSALQKKSQTNKFIEPYEEEEKFLQ       493
LCB2          YCPSKM--------------PAFSRM-MLQRRIAV--VVVAYPATP-LVE       492
HEM1$YEAST    DLAKQASDILINKHQIYVQAINFPTVARGTERLRITPTPGHTNDLSDILI       477
              ...             *  .      .      ..
```

FIGURE 7B

```
              *  *              *                    *         *    *      *    *
LCB1          SIVDHALINYNVLITRN----TIVLKQETLPIVPSLKICCNAAMSPEELK      539
LCB2          SRVRFCMSA--SLTKED----IDYLLRHVSEVGDKLNLKSNSGKSSYDGK      536
HEM1$YEAST    NAVDDVFNELQLPRVRDWESQGGLLGVGESGFVEESNLWTSSQLSLTNDD      527
              . *    . .         .            *         . ..   ..      *    . .

*  *             *
LCB1          NA---CESVKQSILACCQESN---K      558
LCB2          RQRWDIEEVIRRTPEDCKDDKYFVN      561
HEM1$YEAST    LNP----NVRDPIVKQLEVSSGIKQ      548
                .          .*    ..       . . .   .
```

METHOD FOR OBTAINING ANTIFUNGAL AND HERBICIDAL COMPOUNDS THAT TARGET THE FIRST COMMITTED STEP IN SHINGOLIPID LONG-CHAIN BASE BIOSYNTHESIS

This application is a continuation of application Ser. No. 07/906,899 filed Jun. 30, 1992, now abandoned.

BACKGROUND OF THE INVENTION

1. Field of the Invention

This invention relates to the isolation of the LCB1 and LCB2 genes of the year *Saccharomyces cervisiae* that encode subunits of the enzyme serine palmitoyltransferase (SPT), the first enzyme leading to synthesis of the long-base component of sphingolipids. The invention further relates to method of using these genes to either inhibit SPT activity or to inhibit synthesis of the enzyme. Furthermore, the invention relates to methods for construction strains of *S. cervisiae* or other organisms that can be used to select and test for compounds that either inhibit SPT activity or to inhibit synthesis of the enzyme.

2. Description of the Background

Sphingolipids are abundant in the membranes of fungi (Brennah, P. J., & Losel, D. M. 1978. Fungal lipids, in *Microbial Physiology,* Rose, A. H. & Morris, P. G., Eds. 17, 47–179, Acad. Press., N.Y.), animals (Seeley, C. C. and Siddiqui, B. 1977; the Glycojungates, Horowitz, M. I. and Pigman, W., eds., Acad. Press, N.Y. 1:495), and higher plants (Laine, R. a., Hsieh, T. C.-Y., & Lester, R. L. Glycophosphoceramides from plants, in *Cell Surface Glycolipids*, p.65, Am. Chem. Soc. Symp. Ser. 128, Am. Chem. Soc. Wash, D.C.) 1980. In spite of much effort, it has been difficult to understand the exact biological role(s) of sphingolipids and their mode of action at the molecular level. In animals, sphingolipids are thought to play a role in such general cellular events as cell-to-cell recognition, regulation of cell growth, and differentiation. The prevalence of sphingolipids suggests that they play vital roles in cells and direct proof that sphingolipids are essential cellular components has been obtained with the discovery of mutants of *S. cervisiae* that absolutely require a sphingolipid long-chain base (see below) for growth (Wells, G. B. and Lester, R. L.; J.Biol. Chem. 258: pages 10200–10203 (1983)) and viability (Pinto, W. J., Wells, G. B., Williams, A. C., Anderson, K. A., Teater, E. C., and Lester, R. L., *Fed. Proc.* 45: 1826 (1986)).

sphingolipids are derivatives of ceramides containing sugars and sometimes phosphates. Ceramides usually contain a fatty acid of 20–26 carbons connected via an amide linkage to a long-chain base. The major long-chain bases and their predominant distribution are:

Sphingosine (animals)
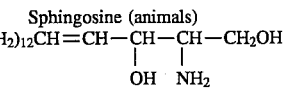

Phytosphingosine (plants, fungi)
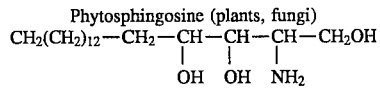

The route of sphingolipid biosynthesis is proposed to be:

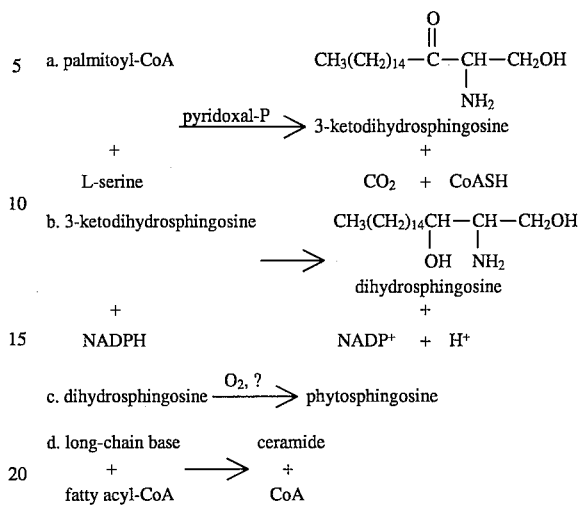

Reaction (a), the first committed step in sphingolipid biosynthesis (reviewed in Merrill, A. H. and Jones, D. D. 1990. *Biochemica et Biophysica Acta.* 1044:1–12) is catalyzed by serine palmitoyltransferase (SPT, also called 3-ketodihydrosphingosine synthetase). This enzyme has been shown to occur in the fungus *Hansenula ciferri* (Snell, E. E., Di Mari, S. J., and Brady, R. N. 1970. *Chem. Phys. Lipids,* 5:116–138), in beef liver (Stoffel, W. 1970. *Chem. Phys. Lipids.* 5:139–158), and in the bacterium *Bacteroides melaninogenicus* (Lev, M., and Milford, A. F. 1973. *Arch. Biochem. Biophys.* 157:500–508). Other evidence for this reaction comes from our own work in *S. cervisiae* (Pinto et al., 1986; Pinto W. J., Wells, G. W. and Lester, R. L. 1992. *J. Bacteriol.* 174:2575–2581). The enzyme has never been purified to homogenity and characterized in any detail (reviewed in Merrill, A. H. and Jones, D. D. 1990. *Biochemica et Biophysica Acta.* 1044:1–12).

In reaction (d) the long-chain base is attached to a fatty acid to form a ceramide. In all organisms ceramides are converted to complex derivatives, the sphingolipids, by the addition of polar groups to the 1-hydroxyl. The sphingolipids in animals contain various oligosaccharides inked glycosidically to the ceramide to yield glycosphingolipids and also contain choline linked by a phosphodiester bond to ceramide to yield the abundant compound sphingomyelin. Certain sphingolipids in fungi and plants differ from the sphingolipids in animals because the 1-hydroxyl is linked through a phosphoryl group to inositol (myo-inositol) rather than directly to a sugar. This core structure, inositol-phosphorylceramide, or inositol-P-ceramide ("IPC", Smith, S. W., and Lester, R. L. 1974. *J. Biol. Chem.* 249:3395–3405), along with mannose-inositol-P-ceramide, (MIPC, ibid) and mannose-(inositol-P)$_2$-ceramide (M(IP)$_2$C, (Steiner, S., Smith, S. Waechter, C. J., and Lester, R. L. 1969. *Proc. Natl. Acad. Sci. U.S.A.* 64:1042–1048) collectively constitute the sphingolipids in *S. cervisiae* (Smith, S. W., and Lester, R. L. 1974. *J. Biol. Chem.* 249:3395–3405). Phosphoinositol sphingolipids are also a major class of lipids in plants (for references see Kaul, K. and Lester, R. L. 1975. *Plant Physiol.,* 55:120–129) and parasites (Singh, B. N., Costello, C. E., and Beach, D. H. 1991. *Arch. Biochem. Biophys.* 286:409–418).

Because sphingolipids are vital for *S. cerevisiae*, the long-chain base biosynthesis pathway would appear to be a good target for antifungal compounds. In fact, sphingolipids may be vital for all organisms that contain them, and therefore, any compound that would inhibit long-chain base biosynthesis might inhibit growth of an organism that contained sphingolipids.

Accordingly, there is a need to begin to identify or design such inhibitory antifungal compounds to target the long-chain base biosynthesis pathway, which would appear to be a good target for antifungal compounds. Therefore we isolated two *S. cerevisiae* genes, LCB1 (SEQ ID NOS.: 1–3) and LCB2 (SEQ ID NOS.: 4–6), that most likely encode subunits of SPT. These are the first genes involved in long-chain base biosynthesis to be isolated from any organism. The genes provide a unique opportunity to identify compounds that block SPT activity or synthesis in specific organisms.

SUMMARY OF THE INVENTION

One objective of the present invention is to provide the LCB1 (SEQ ID NOS.: 1–3), and the LCB2 ((SEQ ID NOS.: 4–6) genes of *S. cerevisiae* and to demonstrate that they provide SPT enzyme activity to a strain that lacks such enzyme activity.

Another objective of the present invention is to provide the LCB1 ((SEQ ID NOS.: 1–3), and the LCB2 ((SEQ ID NOS.: 4–6), genes of *S. cerevisia* for use in constructing a genetically engineered strain of *S. cerevisiae* that has increased SPT protein and therefore enzyme activity.

Another objective of the present invention is to provide the DNA sequence of the LCB1 ((SEQ ID NOS.: 1–3) and LCB2 ((SEQ ID NOS.: 4–6) genes for use as targets for antisense or triple-helix-forming oligonucleotides which will inhibit the production of SPT protein.

Another objective of the present invention is to provide the DNA sequence of the LCB1 (SEQ ID NOS.: 1–3) and LCB2(SEQ ID NOS.: 4–6) genes for use in overexpression of the genes and subsequent overproduction of the SPT enzyme.

Another objective of the present invention is to provide the DNA sequence of the LCB1 ((SEQ ID NOS.: 1–3) and LCB2 ((SEQ ID NOS.: 4–6) genes for use in isolating the homolog of these genes from other organisms.

Other objectives and advantages of the invention will become apparent as the description thereof proceeds.

In satisfaction of the foregoing objects and advantages, the present invention provides the LCB1 ((SEQ ID NOS.: 1–3) and LCB2 ((SEQ ID NOS.: 4–6) genes and their DNA sequence. The genes are shown to restore SPT activity to a lcb1((SEQ ID NOS.: 1–3)-defective and lcb2((SEQ ID NOS.: 4–6)-defective strain, respectively.

BRIEF DESCRIPTION OF THE DRAWINGS

FIG. 2 sets forth the DNA sequence of the LCB1 (SEQ ID NOS.: 4–6) gene and the predicted protein product.

FIG. 3 sets forth a comparison of the LCB1 (SEQ ID NOS.: 1–3) protein sequence with other proteins that catalyze a chemical reaction that is similar to the one catalyzed by SPT.

FIG. 4 sets forth a comparison of the reaction catalyzed by SPT and other enzymes.

FIG. 5(A–C) represents a schematic diagram of plasmids carrying the LCB2 (SEQ ID NOS.: 4–6) gene of *S. cerevisiae* or portions of the gene.

FIG. 6 sets forth the DNA sequence of the LCB2 (SEQ ID NOS.: 4–6) gene and the predicted protein sequence.

FIG. 7 sets forth a comparison of LCB1 (SEQ ID NOS.: 1–3), LCB2 (SEQ ID NOS.: 4–6), and the *S. cerevisiae* HEM1 protein sequences.

DESCRIPTION OF THE PREFERRED EMBODIMENTS

Figure 1:
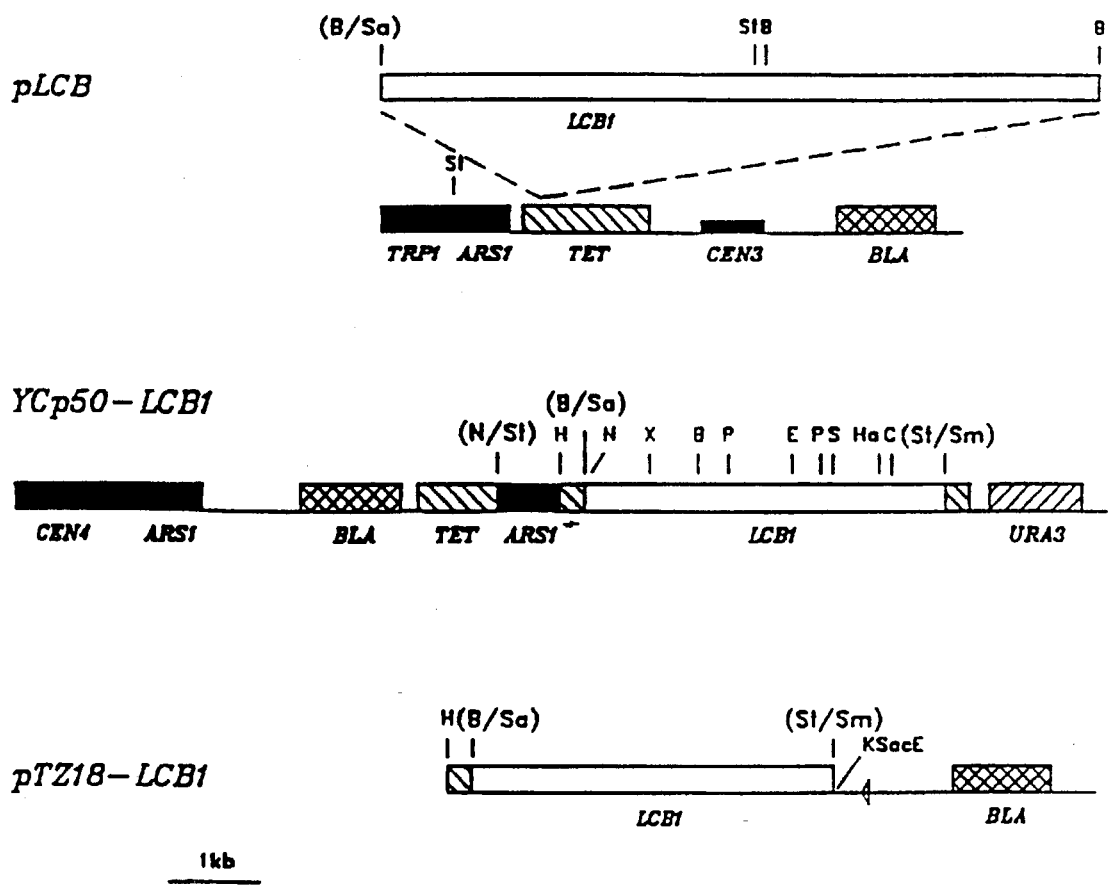
FIG. 1 represents a schematic diagram of plasmids carrying the LCB1 (SEQ ID NOS.: 1–3) gene of *S. cerevisiae*.

The invention relates to the isolation of the LCB1 (SEQ ID NOS.: 1–3) and LCB2 (SEQ ID NOS.: 4–6) genes of *S. cerevisiae*.

The present invention provides a DNA sequence LCB1 having a nucleotide sequence as set forth in FIG. 2. It also provides a plasmid comprising the LCB1 sequence according to the invention. Particularly preferred is a plasmid according to the invention which is the plasmid pTZ18-LCB1 (SEQ ID NOS.: 1–3) containing the LCB1 (SEQ ID NOS.: 1–3) sequence. Also, particularly preferred is a plasmid according to the invention which is plasmid YIpLCB1-1 containing the LCB1 sequence.

In another embodiment the present invention provides a host cell line transformed by a plasmid containing the LCB1 (SEQ ID NOS.: 1–3) sequence according to the present invention.

In another aspect the present invention provides a DNA sequence LCB2 (SEQ ID NOS.: 4–6) having a nucleotide sequence as set forth in FIG. 6. It also provides a plasmid comprising the LCB2 (SEQ ID NOS.: 4–6) sequence according to the invention. Particularly preferred is a plasmid according to the invention which is the plasmid pRSLCB2-2 containing the LCB2 (SEQ ID NOS.: 4–6) sequence.

In another embodiment the present invention provides a host cell line transformed by a plasmid containing the LCB2 (SEQ ID NOS.: 4–6) sequence according to the present invention.

The present invention further provides a genetically engineered strain of *S. cerevisiae* which has increased production of Serine Palmitoyltransferase protein and therefore increased enzyme activity as compared to the wild type *S. cerevisiae*.

In another aspect the present invention provides an antisense or triple helix forming oligonucleotide specific for the LCB1 (SEQ ID NOS.: 1–3) sequence, which will inhibit the production of Serine Palmitoyltransferase protein.

In still another aspect the present invention provides an antisense or triple-helic-forming oligonucleotide specific for the LCB2 (SEQ ID NOS.: 4–6) sequence, which will inhibit the production of Serine Palmitoyltransferase protein.

The present invention also provides a genetically engineered microbial strain transformed by a plasmid comprising either the LCB1 (SEQ ID NOS.: 1–3) or LCB2 (SEQ ID NOS.: 4–6) sequence, or both the LCB1 (SEQ ID NOS.: 1–3) and LCB2 (SEQ ID NOS.: 4–6) sequences, which overexpresses the gene(s) with which it is transformed and subsequently overproduces the Serine Palmitoyltransferase enzyme.

Also the present invention provides a method for testing an oligonucleotide or organic compound for the ability to block Serine Palmitoyltransferase activity or synthesis, which method comprises:

exposing the oligonucleotide or the organic compound being tested to a host cell or host cell extract, which host cell has been transformed to include either a LCB1 (SEQ ID NOS.: 1–3) gene or LCB2 (SEQ ID NOS.: 4–6) gene (or both genes), and testing for an absence of Serine Palmitoyltransferase enzyme or its activity, which diminished activity is indicated by the absence or lower concentration of sphingolipids.

The present invention further provides an oligonucleotide DNA sequence, which is a complement to either the LCB1 (SEQ ID NOS.: 1–3) or LCB2 (SEQ ID NOS.: 4–6) sequences, or to portions thereof.

In yet another aspect the present invention provides a method of testing for and/or isolating closely related sequences (similar to LCB1 (SEQ ID NOS.: 1–3)) which comprises producing or obtaining an oligonucleotide which is a complement to a portion of the LCB1 (SEQ ID NOS.: 1–3) gene, and using the complement as an oligonucleotide probe by exposing a target nucleotide sequence to the said nucleotide probe and testing for binding to said probe, and optionally isolating and separating the nucleotide probe from the DNA sequence to which it has bound.

In still another aspect, the present invention provides a method of testing for and/or isolating closely related sequences (similar to LCB2 (SEQ ID NOS.: 4–6)) which comprises producing or obtaining an oligonucleotide which is a complement to a portion of the LCB2 (SEQ ID NOS.: 4–6) gene, and using the complement as an oligonucleotide probe by exposing a target nucleotide sequence to the said nucleotide probe and testing for binding to said probe, and optionally isolating and separating the nucleotide probe from the DNA sequence to which it has bound.

The LCB1 (SEQ ID NOS.: 1–3) and LCB2 (SEQ ID NOS.: 4–6) sequences according to the present invention, plasmids comprising either of the LCB1 (SEQ ID NOS.: 1–3) or LCB2 (SEQ ID NOS.: 4–6) sequences, transformed host cells having a sequence according to the present invention, and sequences which are complements are all useful in screening potential antifungal agents, or for producing reagents useful in screen potential antifungal agents, (both oligonucleotides and organic chemical agents, which are potential antifungal agents may be screened).

The sequences according to the present invention are also useful to provide oligonucleotides which have complementary DNA sequences, which complementary sequences can be used as probes to screen for sequences which are homologs of the claimed sequences and/or used in a process to isolate and ultimately sequence such homologs of LCB1 (SEQ ID NOS.: 1–3) or LCB2 (SEQ ID NOS.: 4–6).

In accordance with present invention, as a preliminary step, a mutant strain of S. cerevisiae blocked in sphingolipid biosynthesis was obtained. For example, strains of S. cerevisiae carrying the mutant allele, lcb1-1, are absolute auxotrophs and grow only when a long-chain base (lcb, phytosphingosine but not sphingosine) is added to the culture medium.

The genes were isolated from a S. cerevisiae genomic DNA library by complementation for growth on medium lacking a long-chain base (such as phytosphingosine) of an lcb1 or an lcb2-defective strain.

The original lcb mutant MCGA (MATα lcb1-1 inol (J. Biol. Chem. 258, 10200–10203 (1983) was crossed with strain W303-1B (MATα ade2-1 can1-100 ura3-1 his3-11,15 trp1-1 leu2-3,112; obtained from R. J. Rothstein, Columbia University). Progeny from this cross were backcrossed to W303-1B, and several offspring were selected for further study, including strains X2A1B (MATa lcb1-1 ura3-1 trp1-1 his3-11,15). Strain SL1 was derived from strain SJ21R (MATa ura3-52 leu2-3,112 ade1 MEL1) by replacement of the LCB1 allele with a mutant allele that was disrupted by inserting a 1.1-kb URA3 DNA fragment at the SalI site of LCB1. The LCB1:: URA3-disrupted allele was prepared by transferring 4.3-kb HindIII-StuI fragment, carrying LCB1, from pLCB to pTZ18 (Pharmacia) cleaved with HindIII and SmaI. The resulting plasmid, pTZ18-LCB1 was cleaved with SalI and ligated with a 1.1-kb URA3 DNA fragment having SalI cohesive ends (obtained from pUC-URA3 cut with SalI) to yield pTZ18-LCB1::URA3.

To replace the LCB1 chromosomal allele with the URA3-disrupted allele, 10 μg of pTZ18-LCB1::URA3 DNA was cleaved with XbaI and ClaI, extracted with phenol, phenol-chloroform, and chloroform and precipitated with ethanol. The DNA was transformed into strain SJ21R with selection for Ura+ transformants. Replacement of the LCB1 chromosomal allele with the URA3-disrupted allele was verified by Southern blot analysis. YIpLCB1-1 was constructed by inserting TRP1 of S. cerevisiae, as a 1.4-kb HindIII fragmentm into the HindIII site of pTZ18-LCB1. YIpLCB1-1 was cleaved at its unique BAMHI site located on the 3'side of LCB1, and the linear DNA was used to transform strain 24D5 with selection for Ura+transformants. Integration at the expected chromosomal location was verified by Southern blotting. Transformants were crossed to strain YPH1 (MATa ura3-52 lys2-801 ade2-101 (See, for example, Genetics, 122, 19–27 (1989)).

The plasmid pLCB was isolated from a S. cerevisiae genomic DNA library carried in a CEN vector. The 6.44-kb vector was pBR322 with a 0.63-kb Sau3A CEN3 DNA fragment inserted into the PvuII site of the vector and a 1.4-kb TRTRP1 ARS1 fragment inserted into the EcoRI site of the vector. The ligations were done with molecules whose ends were made blunt ended so that the original restriction sites were destroyed. Sau3A genomic DNA fragments of 8-kb average size from strain X2180 (a/α gal2/gal2) were cloned into the BamHI site of the vector (the library was obtained from ZymoGenetics, Seattle, Wash.). DNA fragments from pLCB were subcloned into YCp50 (see, Methods Enzymol., 152, 481–504 (1987)).

Plasmids were propagated in *Escherichia coli* DH5α. The lcb-defective strains were propagated in several media as described later in the detailed section which follows.

For example, to isolate LCB1, strain X2A1B (relevant genotype lcb1-1, trp1) was transformed with a genomic DNA library which was carried in a vector containing CEN3 and ARS1, for single-copy propagation in yeast cells, and TRP1, for selection of Trp$^+$ yeast that had been transformed with the vector. Ten thousand Trp$^+$ transformants were selected on minimal medium plates containing phytosphingosine but lacking tryptophan. Transformants were pooled and reselected on minimal medium plates lacking both tryptophan and phytosphingosine. About one per thirty-five hundred Trp$^+$ colonies was able to grow without added phytosphingosine and thus had an Lcb$^+$ phenotype.

Plasmid DNA was isolated from several Lcb$^+$ yeast transformants and transformed into *E. coli* with selection for ampicillin resistant cells. Plasmid DNA from *E. coli* transformants was isolated and digested with restriction endonucleases. The pattern of restriction fragments indicated that the original Lcb⁺ yeast transformants all contained the same plasmid which carried an insert of about 8 kb.

To localize the LCB1 gene on the 8 kb DNA insert we subcloned parts of the insert into the CEN4 vector YCp50 and tested the resulting plasmids for their ability to confer a Lcb⁺ phenotype on strain X2A1B. The experiments localized LCB1 to a subclone of 4.0 kb (FIG. 1).

Further localization of LCB1 was achieved by chromosomal disruption. For these experiments the 4 kb insert was disrupted at the unique SalI site (FIG. 1) by insertion of the URA3 gene of *S. cerevisiae* to create the lcb1::URA3-disruption allele. The lcb1::URA3-disruption allele was used to replace the wild type LCB1 allele in strain SJ21R (relevant phenotype Lcb⁺ Ura⁻) by homologous recombination as described in EXAMPLE 2. These procedures produced a strain, SL1, having the chromosome disrupted at the expected SalI site. If this procedure had disrupted the LCB1 gene then the strain SL1 should require long-chain base (phytosphingosine) for growth and, therefore, having an Lcb⁻ phenotype. This expectation was verified because strain SL1 had an Lcb⁻ phenotype. We conclude that the SalI site shown in plasmid YCp50-LCB1 between the PstI and HpaI sites is located within the LCB1 gene.

Genetic complementation analysis was used to verify that the lcb1::URA3 disruption mutation in strain SL1 was allelic to the original lcb1-1 mutation carried in strain X2A1B. Strain SL1 was crossed to strain 24D5. The resulting diploids had an Lcb⁻ phenotype, suggesting allelism of the cloned gene and lcb1. Strong support for allelism would be obtained by sporulating these diploids and showing that all tetrads give four Lcb⁻ spores. However, such diploids failed to sporulate under a variety of conditions suggesting that sphingolipids are needed for sporulation. An alternative genetic approach was used to demonstrate allelism. The putative LCB1 allele, carried on the integrating vector YIpLCB1-1, was directed to integrate into its homologous chromosomal locus as described in EXAMPLE 3. The host strain for integration of YIpLCB1 was strain 24D5 which carried the lcb1-1 mutation. If YIpLCB1-1 did indeed carry the wild type LCB1 gene then the host strain should have this plasmid integrated next to the lcb1-1 allele. When this strain is crossed to an LCB1 strain (YPH1) all progeny should be Lcb⁺ since YIpLCB1-1 should be tightly linked to lcb1-1 and there should be little if any recombination events that would separate the two alleles. In fourteen four-spored tetrads from such a cross, showing 2⁺:2⁻ segregation for the Ade, Ura and Leu phenotypes, all spores were Lcb⁺ indicating that YIpLCB1 had been directed to integrate in close proximity to the lcb1-1 allele. We conclude that the LCB1 gene has been cloned and is carried on pTZ18-LCB1 gene as claimed.

To determine if SPT activity was missing in lcb1-defective strains and to determine if a plasmid carrying LCB1 restored such activity we assayed membranes for the enzyme. The parental strain MC6A contained 54.4 units of enzyme activity per mg of protein while the lcb1-defective strain X2A1B contained 2.5 units per mg of protein or about 20 times less enzyme activity that the parental strain: this level of activity is at the limit of detection and the actual enzyme activity may be lower. The cloned LCB1 allele carried in pLCB was able to restore enzyme activity to about 50% of the wild-type level since three independent transformants of strain X2A1B gave 22.7, 25.6, and 22.8 units of enzyme activity per mg of protein. These data support the claim that LCB1 encodes the SPT enzyme or a subunit of the enzyme.

Based upon the results of the lcb1::URA3 disruption experiments a region surrounding the SalI site shown in FIG. 1 was subjected to DNA sequence analysis and the sequence was analyzed by computer to locate large open reading frames which could encode the LCB1 protein. The sequence (FIG. 2) contained a single, large open reading frame, encoding 558 amino acids which was oriented in the same direction of transcription as the LCB1 mRNA (data not shown). This region must code for the LCB1 protein product because it is in the correct 5' to 3' orientation, because a URA3 disruption of the open reading frame at the unique SalI site created a Lcb⁻ phenotype, and because it is genetically tightly linked to the lcb1-1 allele.

The nucleotide sequence of the open reading frame was used to product the amino acid sequence of the LCB1 peptide. The results of the prediction are illustrated above each codon of the nucleotide sequence (FIG. 2) beginning with the first ATG codon at position +1 and ending with the stop codon TAA at position +1675. Assuming that this ATG codon is the true translation initiation site, the product of the open reading frame is a protein of 558 amino acids. Since the amino terminus of the LCB1 protein has not been determined directly it is possible that the amino terminus of the actual protein is different than indicated in FIG. 2. The difference could occur either because of post-translational processing or because an ATG codon down stream of the one shown in FIG. 3 is used as the initiation codon.

Because SPT activity is present in the membrane fraction of lysed cells, we expected the LCB1 protein to be membrane-associated. The hydrophobicity of the deduced protein sequence was therefore examined for potential membrane spanning regions. According to the 5theory of Kyte, J., and Doolittle, R. F. 1982. *J. Mol. Biol.* 157:105–132, the Grand Average Hydropathy Score (GRAVY) for the predicted LCB1 protein is −1.39, a value that places the protein in the same class as globular proteins. A globular, rather than integral membrane, protein is also predicted by the procedure of Eisenberg, D., Schwartz, E., Komaromy, M., and Wall, R. 1984. *J. Mol. Biol.* 179:125–142. In addition, this analysis predicts two very hydrophobic, membrane-associated helices. Helix I spans amino acid residues 12–32 and has the sequence IPIPAFIVTTSSYLWYYFNLV, while Helix II spans residues 344–373 and has the sequence ATAIDITVGSMATALGSTGGFVLG.

The predicted amino acid sequence of the LCB1 protein shows high similarity to the enzyme 5-aminolevulinic acid synthase (ALA synthase) whose structural gene has been sequenced from many organisms including *S. cerevisiae* (ALSY (SEQ ID NO.: 12), FIG. 3, Urban-Grimal, D., Wollard, C., Garnier, T., Dehoux, P., and Labbe-Boise, R. 1986. *Eur. J. Biochem.* 156:511–519), mouse (ALSM (SEQ ID NO.: 10), FIG. 3, Schoenhaut, D. S., and Curtis, P. J. 1986. *Gene* 48:55–63) and chicken (ALSC (SEQ ID NO.: 11), FIG. 3, Riddle, R. D., Yamamoto, M., and Engel, J. D. 1989. *Proc. Natl. Acad. Sci. U.S.A.* 86:792–796). The predicted LCB1 protein also shows high similarity to the *Escherichia coli* enzymes 2-amino-3-ketobutyrate CoA ligase (EKBL (SEQ ID NO.: 8), FIG. 3, Aronson, B. A., Ravnikar, P. D., and Somerville, R. L. 1988. *Nucleic Acids Res.* 16:3586) and biotin synthetase (EBIO, FIG. 3, Otsuka, A. J., Buoncristiani, M. R., Howard, P. K., Flamm, J., Johnson, C., Yamamoto, R., Uchida, K., Cook, C., Ruppet, J., and Matsuzaki, J. 1988. *J. Biol. Chem.* 263:19577–19585).

The similarity of the LCB1 protein to ALA synthase and to 2-amino-3-ketobutyrate CoA ligase seems particularly significant since these enzymes catalyze a reaction (FIG. 4) that is very similar to that catalyzed by SPT. In addition, the *E. coli* 2-amino-3-ketobutyrate CoA ligase uses pyridoxal phosphate as a cofactor (Mukherjee, J. J., Dekker, E. E. 1987. *J. Biol. Chem.* 262:14441–14447) as do serine palmitoyltransferase (Brady, R. O. and Koval, G. J. 1957. *J. Am. Chem. Soc.* 79:2648–2649) and ALA synthase (Warnich, G. R., and Burnham, B. F. 1971. *J. Biol. Chem.* 246:6880–6885). The similarity of the amino acid sequences (FIG. 3) and the reactions catalyzed by these enzymes (FIG. 4) argue that the product of LCB1 is most likely SPT or a catalytic subunit of the enzyme, rather than a regulatory protein that regulates transcription of LCB1 or the enzymatic activity of SPT.

Besides lcb1-mutant strains, lcb2-mutant strains also lack SPT enzyme activity (Pinto, W. J., Wells, G. W., and Lester, R. L. 1992. *J. Bateriol.* 174:2575–2581). The LCB2 gene was isolated from a *S. cerevisiae* genomic DNA library of complementation for growth on medium lacking phytosphingosine of the lcb2 mutation carried in strain BS238. The strain was transformed with the same recombinant DNA library that was used for isolation of LCB1. Ura$^+$ transformants were selected, pooled, and replated on plates lacking phytosphingosine to select transformants that could grow in the absence of phytosphingosine (Lcb$^+$). Plasmid DNA was recovered from Lcb$^+$ cells by transformation into *E. coli*. Plasmid DNA isolated from *E. coli* was analyzed by restriction digestion. The pattern of restriction fragments indicated that all plasmids carried the same insert of about 7-kb which we designated B7 (FIG. 5).

LCB2 was localized by subcloning and testing the subclones for their ability to complement the lcb2 mutation in strain BS238 and allow the strain to grow in the absence of phytosphingosine (EXAMPLE 4). These data localized the LCB2 gene to a region near the ApaI site shown in FIG. 1. DNA around this site was sequenced and the sequence was scanned by computer in all reading frames. There was only one large open reading frame, indicated by the open box at the top of FIG. 5. The determined DNA sequence and the translated open reading frame representing the putative LCB2 protein are indicated in FIG. 6.

To prove that this open reading was the LCB2 gene we used the cloned gene to make a chromosomal deletion allele lcb2Δ3::URA3 (EXAMPLE 5), as shown in FIG. 5. The deletion allele was originally introduced into the diploid strain YPH501 and Southern blotting was used to verify that the deletion strain carried one normal allele and the deletion allele (data not shown). The diploid was sporulated and spores were tested for their Lcb phenotype. All 17 four-spored tetrads showed 2:2 segregation for the Lcb$^+$:Lcb$^-$ phenotype and all the Lcb$^-$ spores were Ura$^+$ as expected for a URA3 gene disruption. Thus, the deleted region is needed for long-chain base synthesis as would be expected if the region was the LCB2 gene. To verify that the putative LCB2 gene indicated in FIG. 5 is allelic to the authentic LCB2 gene, we used the integrating vector pRSLCB2-2 (EXAMPLES 6 and FIG. 5) which only carries the 5' half of the putative LCB2 gene. The plasmid was directed, by digestion with NaiI, to integrate into the genome of strain BS238 (relevant genotype lcb2), at the homologuos NsiI site located in the putative LCB2 gene. Integration at the correct chromosomal location was verified by Southern blotting (data not shown). The strain carrying the integrated plasmid was crossed to strain YPH-500, diploids were selected, and sporulated. Twenty-five four-spored tetrads gave 2 Lcb$^+$:2 Lcb$^-$ segregation and all of the Lcb$^+$ spores were Leu$^-$ while the Lcb$^+$ spores were Leu$^+$. These data demonstrate that the cloned DNA fragment directs integration at or near the lcb2 allele carried in strain BS238. Taken as a whole the data demonstrate that the LCB2 gene has been cloned.

The predicted sequence of the LCB2 protein is shown in FIG. 6. The protein contains 561 amino acid residues. Since the amino terminus of the LCB2 protein has not been determined directly it is possible that the amino terminus of the actual protein is different than indicated in FIG. 6. The difference could occur either because of post-translational processing or because an ATG codon down stream of the one shown in FIG. 6 is used as the initiation codon. A membrane-associated helix is predicted for residues 57 to 77 (PYYIS-LLTYLNYLILIILGHV) and 443–463 (LGFIVYGVAD-SPVIPLLLYCP) by the algorithm of Eisenberg et al., (1984).

Comparison of the LCB2 protein sequence against other sequences in GenBank using the FASTA search procedure of Pearson, W. R. and Lipman, D. J., 1988, *Proc. Natl. Acad. Sci. U.S.A.* 85:2444–2448 revealed that the sequence was homologous to the LCB1 protein and to various ALA synthases including the one from *S. cerevisiae* (FIG. 7). In addition, the sequence was homologuos to the BAC-BIOXWF (Genbank) and the ECOKBLTDH (Genbank, called EKBL (SEQ ID NO.: 8) in FIG. 3) sequences (data not shown).

The similarity of the LCB2 protein to the ALA synthases and to 2-amino-3-ketobutyrate CoA ligase (EKBL FIG. 3, ECOKBLTDH Gen Bank) seems particularly significant since these enzymes catalyze a reaction (FIG. 4) that is very similar to that catalyzed by SPT. In addition, the *E. coli* 2-amino-3-ketobutyrate CoA ligase uses pyridoxal phosphate as a cofactor (Mukherjee and Dekker, 1987) as do serine palmitoyltransferase and ALA synthase. The similarity of the amino acid sequences (FIG. 6) and the reactions catalyzed by these enzymes (FIG. 4) argue that the product of LCB2 is most likely SPT or a catalytic subunit of the enzyme, rather than a regulatory protein that regulates transcription of LCB2 or the enzymatic activity of SPT.

Potential uses of the LCB1 and LCB2 genes.

One use of the genes is to construct strains of *S. cerevisiae* or other organisms or cell lines that can be used to screen for inhibitors of SPT enzyme activity or inhibitors of expression of the LCB1 or LCB2 gene at the transcriptional or translational level. To construct a strain for screening inhibitors of SPT activity, one can use the LCB1 and LCB2 genes to overproduce their protein product. Overproduction will yield a host organism relatively more resistant to SPT inhibitors compared to a host that does not overproduce the proteins. This principle was first demonstrated in *S. cerevisiae* by Rine, J., Hansen, W., Hardeman, E., and Davis, R. W. 1983. *Proc. Natl. Acad. Sci. U.S.A.* 80:6750–6754. In the case of an inhibitor of transcription or translation, for example a triple helix-forming oligonucleotide or an antisense koligonucleotide, one can construct a strain carrying multiple copies of the LCB1 and LCB2 genes. Multiple copies should make the strain more resistant to the inhibitor than a strain having only one copy of each gene. A variation of this approach could be used for inhibitors of translation (an antisense oligonucleotide) in which the LCB1 and LCB2 coding regions would be fused to a strong promoter-enhancer region so that a single copy of the fusion genes would give high levels of LCB1 and LCB2 mRNA.

Another use of the LCB1 and LCB2 genes is to overexpress them and overproduce their protein product. Such overproduction usually makes it possible to purify the proteins. Expression and overproduction could be achieved in any number of organisms including *E. coli*, *S. cerevisiae*, or insect cells or other hosts for baculovirus vectors. The purified protein could then be used to identify or design inhibitors of SPT enzyme activity.

Finally, the LCB1 and LCB2 genes can be used to isolate their homologs from other organisms. Homologs can be isolated by complementation of the lcb1 and lcb2 mutation in appropriate *S. cerevisiae* host strains such as those presented in this application. Alternatively, degenerate primers for the polymerase chain reaction (PCR) could be designed based upon the sequence of LCB1 and LCB2 and used to prime a PCR reaction using genomic or cDNA from the organism whose LCB genes are to be cloned. LCB1 and LCB2 homologs from particular organisms would enable the design of highly specific triple-helix forming or antisense oligonucleotides or for inhibitors of SPT activity unique to a particular organism.

In the examples the following materials were used:

*S. cerevisiae:* The original lcb mutant MC6A (MATa lcb1-1 inol; Wells and Lester, 1983), was crossed with strain W303-1B (MATa ade2-1 can1-100 ura3-1 his3-11,15 trp1-1 leu2-3,112; obtained from R. J. Rothstein, Columbia, Univ.). Progeny from this cross were backcrossed to W303-1B and several offspring were selected for further study including strains X2A1B (MATa lcb1-1 ura3-1 trp1-1 his3-11,15) and 24D5 (MATα lcb1-1 ura3-1 trp1-1 leu2-3,112 his3-11,15). Strains YPH1(MATa ura3-52 lys2-801 ade2-101,), YPH500 (MATa ura3-52 leu2-801$^{amber}$ leu2-Δ101$^{ochre}$ trp1-Δ63 his3-Δ20 leu2-Δ1), and YPH501 (MATa/a ura3-52 leu2-801$^{amber}$ leu2-101$^{ochre}$ trp1-Δ63 his3Δ20 leu2-d1, were obtained from Sikorski, R. S. and Hieter, P., 1989, *Genetics*, 122:19–27. Strain BS238 (MATa lcb2 ura3-52 leu2-3,112 ade1) was from Pinto, W. J., Srinivasan, B., Shepherd, S., Schmidt, A., Dickson, R. C., and Lester, R. L. 1992. *J. Bacteriol.* 174:2565–2574. Strain SJ21R (MATa ura3-52 leu2-3,112 ade1 MEL1) was described in Dickson, R. C., Wells, G. B., Schmidt, A., and Lester, R. L. 1990. *Mol. Cell. Biol.* 10:2176–2181. The YPH strains are sensitive to the long-chain base phytosphingosine and in order to transform them with DNA it is necessary to use 12.5 μM phytosphingosine and 0.025% tergitol (half of the normal concentrations) in selection plates. Likewise, for genetic crosses involving YPH strains it is necessary to make the same adjustments for dissection plates (minimal medium, Sherman, F., Fink, G. R., and Hicks, T. B. 1986. *Methods in Yeasts Genetics*, Cold Spring Harbor Laboratory, Cold Spring Harbor, N. Y.) otherwise spores will not germinate.

*Escherichia coli:* strain DH5α was used for propagation of plasmids.

Media: PYED contained 1% peptone, 1% yeast extract, 2% agar (for plates), 50 mM sodium succinate (pH 5), inositol (50 mg/l), potassium phosphate monobasic (50 mg/ml), and 2% or 4% glucose. Minimal medium contained 1× Difco Yeast Nitrogen Base without amino acids, 50 μM sodium succinate (pH 5), 2% glucose, 1.5% agar (for plates), inositol (50 mg/ml), valine (150 mg/ml), isoleucine (30 mg/ml), threonine (200 mg/ml) and these supplements at 20 mg/l: adenine sulfate, arginine-HCl, histidine-HCl, leucine, lysine-HCl, methionine, tryptophan, and uracil. One or more supplements were omitted from minimal medium for selection of yeast transformants. For strains requiring long chain base the medium was supplemented with 25 μM phytosphingosine (Sigma, St. Louis, Mo.). A 10× stock solution of phytosphingosine was prepared by adding 0.25 ml of 100 μM phytosphingosine (dissolved in 95% ethanol) to 99.75 ml of a 0.5% solution of tergitol (Sigma, St. Louis, Mo.).

DNA sequencing: Synthetic oligonucleotide primers were used for dideoxynucleotide sequencing with Sequenase Version 2.0 DNA Polymerase (USB, Cleveland, Ohio) essentially as recommended by the supplier. The LCB1 sequence (FIG. 2) has been deposited in the Gen Bank and given accession number M63674. The LCB2 sequence (FIG. 6) has been deposited in the Gen Bank and given accession number M95669.

Serine palmitoyltransferase activity assays were done as described in Buede, R., Rinker-Schaffer, C., Pinto, W. J., Lester, R. L., and Dickson, R. C. 1991. *J. Bacteriol.* 173:4325–4332.

Miscellaneous Procedures—Yeast were transformed by the lithium acetate procedure described by Sherman, F., Fink, G. R., and Hicks, T. B. 1986. *Methods in Yeasts Genetics*, Cold Spring Harbor Laboratory, Cold Spring Harbor, N.Y. Genetic crosses and tetrad analysis were done by standard procedures (ibid). Southern blots were done essentially as described by Maniatis, T., Fritsch, E. F., and Sambrook, J. 1982. *Molecular Cloning: A Laboratory Manual,* Cold Spring Harbor Laboratory, Cold Spring Harbor, N.Y. For Southern blots [$^{32}$P]dATP-labeled probes were prepared by the method of Feinberg, A. P., and Vogelstein, B. 1983. *Anal. Biochem.* 132:6–13.

EXAMPLE 1

The plasmid pLCB (FIG. 1) was isolated from a *S. cerevisiae* genomic DNA library carried in a vector containing the CEN3 region of *S. cerevisiae* DNA. The 6.44 kb vector was pBR322 with a 0.63 kb Sau3A CEN3 DNA fragment inserted into the PvuII site of the vector and a 1.4 kb TRP1ARS1 fragment inserted into the EcoRI site of the vector. These ligations were done with molecules whose ends were made blunt-ended so that the original restriction sites were destroyed. Sau3A genomic DNA fragments of 8 kb average size from strain X2180 (a/a gal2/gal2) were cloned into the BamHI site of the vector (the library was a gift from Zymogenetics, Seattle, Wash.). To construct YCp50-LCB1, a 4.7 kb StuI fragment from pLCB1 containing the LCB1 region, was subcloned into the NruI site of YCp50 (Rose, M. D. 1987. *Meth. Enzymology.* 152:481–504).

EXAMPLE 2

Strain SL1 as derived from strain SJ21R by replacement of the LCB1 allele with a mutant allele that was disrupted by inserting a 1.1 kb URA3 DNA fragment from *S. cerevisiae* into the SalI site of LCB1 (FIG. 1 shows the SalI site). The lcb1::URA3 -disrupted allele was prepared by ligating a 4.3 kb HindIII-StuI fragment, carrying LCB1, derived from pLCB (FIG. 1) to pTZ18 (Pharmacia) which had been cleaved with the restriction endonucleases HindIII and SmaI. The resulting plasmid, pTZ18-LCB1 (FIG. 1), was cleaved with SalI and ligated with a 1.1 kb URA3 DNA fragment having SalI cohesive ends to yield pTZ18-LCB1::URA3. To replace the LCB1 chromosomal allele with the URA3-disrupted allele, ten micrograms of pTZ18-LCB1::URA3 DNA was cleaved with XbaI and ClaI, extracted with phenol, phenol:chloroform and chloroform, and precipitated with ethanol. The DNA was transformed into strain SJ21R with selection for Ura$^+$ transformants. Replacement of the LCB1 chromosomal allele with the URA3-disrupted allele was verified by Southern blot analysis. Total DNA isolated from SL1 and the non-disrupted parental strain SJ21R was cleaved with the restriction endonucleases NruI and StuI. Following Southern blot analysis, the parental strain showed a 4 kb band of hybridization, as expected, when the blot was probed with a $^{32}$P-labeled NruI to StuI DNA probe containing the LCB1 region (FIG. 1). If the lcb1::URA3-disrupted allele had replaced the wild type allele of LCB1 in strain SL1 then the Southern blot of strain SL1 should show two bands that hybridize to the $^{32}$P-probe because URA3 contains a StuI cleavage site. The fragments should be 2.1 kb and 3 kb in length. The Southern blot (data not shown) contained the two expected bands of hybridization indicating that strain SL1 carried the lcb1::URA3-disruption allele.

EXAMPLE 3

YIpLCB1-1 was constructed by inserting TRP1 of S. cerevisiae, as a 1.4 kb Hind III fragment, into the Hind III site of pTZ18-LCB1. YIpLCB1-1 was cleaved at its unique BamHI site (FIG. 1), located on the 3' side of LCB1, and the linear DNA was used to transform strain 24D5 with selection for Ura$^+$ transformants. Integration at the expected chromosomal location was verified by southern blotting. Transformants were crossed to strain YPH1.

EXAMPLE 4

Plasmids carrying all of or portions of LCB2 (FIG. 2) were constructed using standard molecular cloning techniques as follows. Insert B7 is a 7 kb BamHI S. cerevisiae DNA fragment cloned into the BamHI site of pRS315 (Sikorski and Hieter, 1989). Insert B7ΔS is a 4.9 kb BamHI-SalI fragment cloned into pRS315 at the BamHI-SalI sites of the polylinker. Insert 2.3 is a 2.3 kb BamHI-SacI fragment cloned into pRS316 (Sikorski and Hieter, 1989) at the BamHI-SacI sites of the polylinker. Insert LCB2-R is a 4.3-kb EcoRI fragment made blunt-ended by filling in the ends with the Klenow fragment of DNA polymerase I and ligated into the SmaI site of pRS315.

EXAMPLE 5

S. cerevisiae strain LCB25, carrying the lcb2Δ3::URA3 allele (FIG. 5), was derived from strain YPH501 as follows: The LCB2-R insert, carried in pIC20R, Marsh, J. L., Erfle, M. and Wykes, E. J., 1984, Gene 32:481–485, at the EcoRI site of the polylinker, was cleaved with the restriction endonucleases ClaI and XbaI (FIG. 5), the ends of the molecules were made blunt by treatment with the Klenow fragment of DNA polymerase I, and the fragment was ligated to a 1.1 kb URA3 fragment having blunt ends to give the lcb2Δ3::URA3 allele (FIG. 5).

EXAMPLE 6

The integrating vector pRSLCB2-2 (FIG. 5) was constructed by cloning a 2.6-kb BamHI-ApaI fragment from the B7 insert into the BamHI-ApaI region of the polylinker in pRS305 (Sikorski and Hieter, 1989). pRS305 carries the LEU2 marker gene that was used for selection of transformants in S. cerevisiae strain BS238.

DETAILED DESCRIPTION OF THE FIGURES

FIG. 1

Structure of Plasmids. The plasmid pLCB carrying the LCB1 gene is shown. The approximate location of LCB1 is indicated. Not all restriction endonuclease sites are indicated in a given plasmid. The open arrowhead in pTZ18-LCB1 represents the T7 promoter. DNA sequences are: open box, S. cerevisiae; TRP1, a marker gene for selection in S cerevisiae; ARS1, a S. cerevisiae autonomous replication sequence; CEN3 a centromere for maintenance of a single-copy of the vector in yeast; BLA and TET confer ampicillin and tetracycline resistance in E. coli, respectively. Abbreviations for restriction endonucleases are: B, BamHI, C, ClaI: E, EcoRI; H, HindIII; Ha, HpaI; K, KpnI; P, PstI; S, SalI; Sa, Sau3A; Sac, SacI; Sm, SmaI; St, StuI; X, XbaI.

FIG. 2

DNA sequence of LCB1. The nucleotide sequence of the LCB1 gene of S. cervisiae is presented along with the deduced protein sequence of the 558 amino acids. The predicted translation start codon is indicated by +1.

FIG. 3

Comparison of the deduced amino acid sequence of LCB1 to other proteins. The protein sequences of LCB1 and the mouse (ALSM ((SEQ ID. NO.:10)), chicken (ALSC ((SEQ ID. NO.:11)), and yeast (ALSY ((SEQ ID. NO.:12)) 5-aminolevulinic acid synthases were compared using the procedure of Pearson and Lipman (1988) and aligned for maximum similarity. The 2-amino-3-ketobutyrate CoA ligase (EKBO ((SEQ ID. NO.:8)) and the biotin synthetase (EBIO ((SEQ ID. NO.:7)) sequences were identified and aligned by using the FASTA algorithm (ibid). Colons (:) represent identity between residues while dots (.) denote conservative replacements by similar residues. Insertions made during the alignment optimization process are indicated by dashes (—).

FIG. 4

Comparison of the reactions catalyzed by serine palmitoyltransferase, ALA synthase, and 2-amino-3ketobutyrate CoA ligase.

FIG. 5

Structure of Plasmids. A restriction map of the 7 kb BamHI fragment carrying the LCB2 gene is shown at the top of the figure and the approximate location of LCB2 and the direction of transcription are indicated. Not all of the cutting sites for a particular restriction endonuclease are indicated. A. Portions of the region carrying LCB2 were tested for their ability to complement the Lcb$^-$ phenotype of an lcb2-defective strain. B. Structure of a deletion allele. C. Structure of the chromosomal insert carried in pRSLCB2-2. Vector sequences are not shown. Abbreviations for restriction endonucleases are: A, ApaI; B, BamHI; C, ClaI; E, EcoRI; Ns, NsiI; Sa, SalI; S, SacI; Sn, SnaBI; Sp, SspI; X, XbaI.

FIG. 6

DNA sequence of LCB2. The nucleotide sequence of the LCB2 gene of S. cervisiae is presented along with the deduced protein sequence of the 561 amino acids. Numbers on the right side of the figure indicate amino acid residues while numbers on the left indicate nucleotides. The A of the predicted ATG initiation codon has been designated as +1.

FIG. 7

Comparison of the predicted LCB1 ((SEQ ID. NO.:13) and LCB2 ((SEQ ID. NO.:14) protein sequences with each other (identical residues indicated by an asterisk above the sequence) and with the ALA synthase of S. cervisiae (HEM1$Yeast ((SEQ ID. NO.:15)). Asterisks below the sequence indicate amino acids that are identical in all three sequences while dots (.) indicate amino acids that are similar in the three sequences. Dashes (—) indicate gaps in the sequence introduced to improve alignment.

The invention now being fully described it will be apparent to one of ordinary skill in the art that many changes and modifications can be made thereto without departing from the spirit or scope of the invention as set forth therein. The foregoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of the disclosed embodiments. It is to be understood that the phraseology or terminology employed herein is for the purpose of description only and not of limitation.

---

What is claimed is:

1. A DNA sequence LCB1 having the nucleotide sequence of Sequence ID NOs: 1–3, wherein LCB stands for long chain base.

2. A plasmid comprising the LCB1 sequence according to claim 1.

3. A plasmid according to claim 2, which is the plasmid pTZ18-LCB1.

4. A plasmid according to claim 2, which is YIpLCB1-1.

5. A host cell transformed by a plasmid to comprise and express an LCB1 sequence according to claim 1.

6. A DNA sequence LCB2 having the nucleotide sequence of Sequence ID NOS: 4–6.

7. A plasmid comprising the DNA sequence according to claim 6.

8. A plasmid according to claim 7, which is pRSLCB2-2.

9. A host cell transformed by a plasmid to comprise and express an LCB2 sequence according to claim 6.

10. A genetically engineered microbial strain transformed by a plasmid comprising both the LCB1 and LCB2 sequences of claims 1 and 6, wherein said plasmid over expresses the genes with which it has transformed and overproduces the Serine Palmitoyltransferase enzyme.

11. A DNA sequence which is a complement to the sequence according to claim 1.

12. A DNA sequence which is a complement to the sequence according to claim 5.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 333
        ( B ) TYPE: Nucleic Acid
        ( C ) STRANDEDNESS: single
        ( D ) TOPOLOGY: linear ( i i ) MOLECULE TYPE: polynucleotide ( x i ) SEQUENCE DESCRIPTION: SEQ ID NO:1:

```
CGCGTATTTT  TTTTTTTTG   AGGCGCCATG  ATTTCTTACA  CGGTTTCTTT  TTTTTTTCCT    60
TCTTTCCTTC  TTGCTTCTCT  GCTAACAAAT  TTTTCACTCA  TTCTTTTTA   TAGGGGCATA   120
TTGCTGCGGT  TAACTGTAGT  GAACGAAAGT  AAGATTGAGA  AAATATAGTA  CTTAAGAAAA   180
AGAAAAGGAA  AAATAAAAAA  AATTCTTTTC  AACATCATCG  AGTAGCACAG  TATAAGAGCG   240
CTCTAACCTT  CTGCCTGGCC  TCCAATATAC  ACATTTGCT   CGTGTAGGGT  TATTTATCCT   300
TTTTTCTTCC  TTCCCACCCA  AAAAAAAAA   GCA                                  333
```

( 2 ) INFORMATION FOR SEQ ID NO:2:

( i ) SEQUENCE CHARACTERISTICS:
        ( A ) LENGTH: 1674
        ( B ) TYPE: nucleic acid
        ( C ) STRANDEDNESS: single
        ( D ) TOPOLOGY: linear ( i i ) MOLECULE TYPE: polypeptide ( x i ) SEQUENCE DESCRIPTION: SEQ ID NO:2:

```
ATG  GCA  CAC  ATC  CCA  GAG  GTT  TTA  CCC  AAA  TCA  ATA  CCG  ATT  CCG  GCA     48
MET  Ala  His  Ile  Pro  Glu  Val  Leu  Pro  Lys  Ser  Ile  Pro  Ile  Pro  Ala
               5              10             15

TTT  ATT  GTT  ACC  ACC  TCA  TCG  TAC  CTA  TGG  TAC  TAC  TTC  AAT  CTG  GTG     96
Phe  Ile  Val  Thr  Thr  Ser  Ser  Tyr  Leu  Trp  Tyr  Tyr  Phe  Asn  Leu  Val
               20             25             30

TTG  ACT  CAA  ATC  CCG  GGA  GGC  CAA  TTC  ATC  GTT  TCG  TAC  ATC  AAG  AAA    144
Leu  Thr  Gln  Ile  Pro  Gly  Gly  Gln  Phe  Ile  Val  Ser  Tyr  Ile  Lys  Lys
          35             40             45

TCG  CAT  CAT  GAC  GAT  CCA  TAC  AGG  ACC  ACG  GTT  GAG  ATA  GGG  CTT  ATT    192
Ser  His  His  Asp  Asp  Pro  Tyr  Arg  Thr  Thr  Val  Glu  Ile  Gly  Leu  Ile
     50             55             60

TTA  TAC  GGG  ATC  ATC  TAT  TAC  TTG  TCC  AAG  CCA  CAA  CAG  AAA  AAG  AGT    240
Leu  Tyr  Gly  Ile  Ile  Tyr  Tyr  Leu  Ser  Lys  Pro  Gln  Gln  Lys  Lys  Ser
65             70             75             80

CTT  CAA  GCA  CAG  AAG  CCC  AAC  CTA  TCG  CCC  CAG  GAG  ATT  GAC  GCG  CTA    288
Leu  Gln  Ala  Gln  Lys  Pro  Asn  Leu  Ser  Pro  Gln  Glu  Ile  Asp  Ala  Leu
               85             90             95

ATT  GAG  GAC  TGG  GAG  CCC  GAG  CCT  CTA  GTC  GAC  CCT  TCT  GCC  ACC  GAT    336
Ile  Glu  Asp  Trp  Glu  Pro  Glu  Pro  Leu  Val  Asp  Pro  Ser  Ala  Thr  Asp
```

|     |     |     |     |     | 100 |     |     |     |     | 105 |     |     |     |     | 110 |     |     |      |
|-----|-----|-----|-----|-----|-----|-----|-----|-----|-----|-----|-----|-----|-----|-----|-----|-----|-----|------|
| GAG | CAA | TCG | TGG | AGG | GTG | GCC | AAA | ACA | CCC | GTC | ACC | ATG | GAA | ATG | CCC |     |     | 384  |
| Glu | Gln | Ser | Trp | Arg | Val | Ala | Lys | Thr | Pro | Val | Thr | MET | Glu | MET | Pro |     |     |      |
|     |     | 115 |     |     |     |     | 120 |     |     |     |     | 125 |     |     |     |     |     |      |

```
      GAG CAA TCG TGG AGG GTG GCC AAA ACA CCC GTC ACC ATG GAA ATG CCC                                384
      Glu Gln Ser Trp Arg Val Ala Lys Thr Pro Val Thr MET Glu MET Pro
              115             120                 125

ATT CAG AAC CAT ATT ACT ATC ACC AGA AAC AAC CTG CAG GAG AAG TAT                                432
      Ile Gln Asn His Ile Thr Ile Thr Arg Asn Asn Leu Gln Glu Lys Tyr
              130             135                 140

ACC AAT GTT TTC AAT TTG GCC TCG AAC AAC TTT TTG CAA TTG TCC GCT                                480
      Thr Asn Val Phe Asn Leu Ala Ser Asn Asn Phe Leu Gln Leu Ser Ala
      145                 150                 155                 160

ACG GAG CCC GTG AAA GAA GTG GTC AAG ACC ACT ATC AAG AAT TAC GGT                                528
      Thr Glu Pro Val Lys Glu Val Val Lys Thr Thr Ile Lys Asn Tyr Gly
                      165                 170                 175

GTG GGC GCC TGT GGT CCC GCC GGG TTC TAC GGT AAC CAG GAC GTT CAT                                576
      Val Gly Ala Cys Gly Pro Ala Gly Phe Tyr Gly Asn Gln Asp Val His
                  180                 185                 190

TAC ACG TTG GAA TAT GAT TTA GCA CAG TTC TTT GGC ACC CAA GGT TCC                                624
      Tyr Thr Leu Glu Tyr Asp Leu Ala Gln Phe Phe Gly Thr Gln Gly Ser
              195                 200                 205

GTT CTG TAC GGG CAA GAC TTT TGT GCC GCA CCC TCT GTT CTG CCT GCT                                672
      Val Leu Tyr Gly Gln Asp Phe Cys Ala Ala Pro Ser Val Leu Pro Ala
              210                 215                 220

TTC ACA AAG CGT GGT GAT GTT ATC GTG GCA GAC GAC CAG GTG TCA TTA                                720
      Phe Thr Lys Arg Gly Asp Val Ile Val Ala Asp Asp Gln Val Ser Leu
      225                 230                 235                 240

CCA GTG CAA AAT GCT CTG CAA CTA AGC AGA TCC ACA GTC TAC TAC TTC                                768
      Pro Val Gln Asn Ala Leu Gln Leu Ser Arg Ser Thr Val Tyr Tyr Phe
                      245                 250                 255

AAC CAC AAC GAT ATG AAT TCG CTA GAA TGT TTA TTA AAC GAG TTG ACC                                816
      Asn His Asn Asp MET Asn Ser Leu Glu Cys Leu Leu Asn Glu Leu Thr
                  260                 265                 270

GAA CAG GAG AAA CTT GAG AAA CTG CCC GCC ATT CCA AGA AAA TTT ATC                                864
      Glu Gln Glu Lys Leu Glu Lys Leu Pro Ala Ile Pro Arg Lys Phe Ile
              275                 280                 285

GTC ACT GAG GGT ATT TTC CAC AAC TCG GGC GAT TTA GCT CCG TTG CCT                                912
      Val Thr Glu Gly Ile Phe His Asn Ser Gly Asp Leu Ala Pro Leu Pro
              290                 295                 300

GAG TTG ACT AAG CTG AAG AAC AAG TAC AAG TTC AGA CTA TTT GTT GAC                                960
      Glu Leu Thr Lys Leu Lys Asn Lys Tyr Lys Phe Arg Leu Phe Val Asp
      305                 310                 315                 320

GAA ACC TTC TCC ATT GGT GTT CTT GGC GCT ACG GGC CGT GGG TTG TCA                                1008
      Glu Thr Phe Ser Ile Gly Val Leu Gly Ala Thr Gly Arg Gly Leu Ser
                      325                 330                 335

GAG CAC TTC AAC ATG GAT CGC GCA ACT GCC ATT GAC ATT ACC GTT GGG                                1056
      Glu His Phe Asn MET Asp Arg Ala Thr Ala Ile Asp Ile Thr Val Gly
                  340                 345                 350

TCC ATG GCC ACC GCG TTG GGG TCC ACC GGT GGT TTT GTC CTG GGT GAC                                1104
      Ser MET Ala Thr Ala Leu Gly Ser Thr Gly Gly Phe Val Leu Gly Asp
              355                 360                 365

AGT GTT ATG TGT TTG CAC CAG CGT ATT GGT TCC AAT GCA TAT TGT TTT                                1152
      Ser Val MET Cys Leu His Gln Arg Ile Gly Ser Asn Ala Tyr Cys Phe
              370                 375                 380

TCT GCC TGT TTG CCG GCT TAC ACC GTC ACA TCC GTC TCC AAA GTC TTG                                1200
      Ser Ala Cys Leu Pro Ala Tyr Thr Val Thr Ser Val Ser Lys Val Leu
      385                 390                 395                 400

AAA TTG ATG GAC TCC AAC AAC GAC GCC GTC CAG ACG CTG CAA AAA CTA                                1248
      Lys Leu MET Asp Ser Asn Asn Asp Ala Val Gln Thr Leu Gln Lys Leu
                      405                 410                 415

TCC AAA TCT TTG CAT GAT TCC TTT GCA TCT GAC GAC TCC TTG CGT TCA                                1296
      Ser Lys Ser Leu His Asp Ser Phe Ala Ser Asp Asp Ser Leu Arg Ser
```

-continued

|  |  |  | 420 |  |  |  | 425 |  |  |  | 430 |  |  |  |
|---|---|---|---|---|---|---|---|---|---|---|---|---|---|---|---|
| TAC | GTA | ATC | GTC | ACG | TCC | TCT | CCA | GTG | TCT | CCT | GTC | CTA | CAT | CTG | CAA | 1344
| Tyr | Val | Ile | Val | Thr | Ser | Ser | Pro | Val | Ser | Pro | Val | Leu | His | Leu | Gln |
|  |  | 435 |  |  |  |  | 440 |  |  |  |  | 445 |  |  |  |
| CTG | ACT | CCC | GCA | TAT | AGG | TCT | CGC | AAG | TTC | GGA | TAC | ACC | TGC | GAA | CAG | 1392
| Leu | Thr | Pro | Ala | Tyr | Arg | Ser | Arg | Lys | Phe | Gly | Tyr | Thr | Cys | Glu | Gln |
|  | 450 |  |  |  |  | 455 |  |  |  |  | 460 |  |  |  |  |
| CTA | TTC | GAA | ACC | ATG | TCA | GCT | TTG | CAA | AAG | AAG | TCC | CAG | ACA | AAC | AAA | 1440
| Leu | Phe | Glu | Thr | MET | Ser | Ala | Leu | Gln | Lys | Lys | Ser | Gln | Thr | Asn | Lys |
| 465 |  |  |  |  | 470 |  |  |  |  | 475 |  |  |  |  | 480 |
| TTC | ATT | GAG | CCA | TAC | GAA | GAG | GAG | GAA | AAA | TTT | CTG | CAG | TCC | ATA | GTA | 1488
| Phe | Ile | Glu | Pro | Tyr | Glu | Glu | Glu | Glu | Lys | Phe | Leu | Gln | Ser | Ile | Val |
|  |  |  |  | 485 |  |  |  |  | 490 |  |  |  |  | 495 |  |
| GAT | CAT | GCT | CTT | ATT | AAC | TAC | AAC | GTT | CTC | ATC | ACA | AGA | AAC | ACT | ATT | 1536
| Asp | His | Ala | Leu | Ile | Asn | Tyr | Asn | Val | Leu | Ile | Thr | Arg | Asn | Thr | Ile |
|  |  |  | 500 |  |  |  |  | 505 |  |  |  |  | 510 |  |  |
| GTT | TTA | AAA | CAG | GAG | ACG | CTA | CCA | ATT | GTC | CCT | AGC | TTG | AAA | ATC | TGC | 1584
| Val | Leu | Lys | Gln | Glu | Thr | Leu | Pro | Ile | Val | Pro | Ser | Leu | Lys | Ile | Cys |
|  |  | 515 |  |  |  |  | 520 |  |  |  |  | 525 |  |  |  |
| TGT | AAC | GCC | GCC | ATG | TCC | CCA | GAG | GAA | CTC | AAA | AAT | GCT | TGC | GAA | AGT | 1632
| Cys | Asn | Ala | Ala | MET | Ser | Pro | Glu | Glu | Leu | Lys | Asn | Ala | Cys | Glu | Ser |
|  | 530 |  |  |  |  | 535 |  |  |  |  | 540 |  |  |  |  |
| GTC | AAG | CAG | TCC | ATC | CTT | GCC | TGT | TGC | CAA | GAA | TCT | AAT | AAA |  |  | 1674
| Val | Lys | Gln | Ser | Ile | Leu | Ala | Cys | Cys | Gln | Glu | Ser | Asn | Lys |  |  |
| 545 |  |  |  |  | 550 |  |  |  |  | 555 |  |  |  |  |  |

( 2 ) INFORMATION FOR SEQ ID NO:3:

( i ) SEQUENCE CHARACTERISTICS:
        ( A ) LENGTH: 463
        ( B ) TYPE: nucleic acid
        ( C ) STRANDEDNESS: single
        ( D ) TOPOLOGY: linear ( i i ) MOLECULE TYPE: polynucleotide ( x i ) SEQUENCE DESCRIPTION: SEQ ID NO:3:

| TAAAAATAGA | AAGCCAGTAT | ATGCACACGC | ACATATATAT | ATAAATATTT | ATACAATAAT | 60 |
| ACAAATAATC | GTAACATCAT | CTCTGTCAAA | TTGACGTGGT | GCACGGCGCC | CAGAGAATGC | 120 |
| GCTAAAAATT | TTCGGATCCG | AAATTTTCTT | TCCTTTTACC | ATCGAGGCAA | AGCAACCTGT | 180 |
| ATTATTTATT | TGTTTATTTA | TTAATAGAAA | AGAAGGAGT | ACTTTCGTGG | TACGCTTTCT | 240 |
| TGAGCATTTT | CGGTTTCACT | AGGCAGAGAA | CTAACACAAG | AGACACAGCA | AACATCAAAC | 300 |
| AAGGTTAAAA | CAGCACACCA | AGGCAATATG | ATGCATTTTA | GAAAGAAATC | CAGTATCAGT | 360 |
| AACACGAGTG | ATCATGACGG | AGCGAACCGT | GCCTCAGATG | TCAAGATTTC | TGAAGATGAC | 420 |
| AAGGCAAGAT | TGAAGATGCG | TACTGCTTCC | GTTGCTGATC | CTA |  | 463 |

( 2 ) INFORMATION FOR SEQ ID NO:4:

( i ) SEQUENCE CHARACTERISTICS:
        ( A ) LENGTH: 884
        ( B ) TYPE: nucleic acid
        ( C ) STRANDEDNESS: single
        ( D ) TOPOLOGY: linear ( i i ) MOLECULE TYPE: polynucleotide ( x i ) SEQUENCE DESCRIPTION: SEQ ID NO:4:

| GCAAATATTG | ATTCTCGATG | AGGCATTTTC | TGGAATGGAG | GTAGAACCTA | TGATGCGTTG | 60 |
| TCATGAATTT | TTAGAGGAGT | GGCCTGGAAC | AGTCCTTGTA | GTGGCACACG | TTGCCGAAGA | 120 |

| | | | | | |
|---|---|---|---|---|---|
| GACACCAAAA | TGTGCCCATT | ACTTAAGGCT | CATATCTCCT | GGAGAGTATG | AAATAGGCGA | 180 |
| TATGGAAAAT | TAAAGTTTTC | TGTTGTGTGG | CAGCAAGAGA | CAGAACCTCG | ATAATTTGAC | 240 |
| ATACGTATAT | AATAGTACAT | GTACATAAAA | ACGTACGCAA | ATATCGTATA | TCTGTTATAC | 300 |
| TACAAAACAA | TTACTTCTAT | ATCATAGCCA | GTTAGCGGGA | ACGACTTCAG | CTAAATGGAC | 360 |
| TATCCATGCT | TTAGGCAGAG | GCGAAGCGCG | GTGATTGGGT | GTAACATCAT | CTCCTTTTCT | 420 |
| CTACGACAAA | TTCCCAAAAA | AAAAATTTAT | GCTATGTTAA | TACCTGCACA | ATTCAACCGT | 480 |
| GCTGAAACGT | AAAATTAAGG | TGATTATACG | GATAGTATAC | GATATTATCA | ATCTCATAAG | 540 |
| AAAAATCTCT | TTTGAATTTA | ACGGAGGGAT | TATTCATTAG | AAAGCGTTCT | TACCATTCAC | 600 |
| TAGGAGCGAA | TCCGTGGAAG | GTGTTTTAAC | GTTGCCACGA | AAAACAGCTC | TACATCGAAA | 660 |
| TAAAAGACAA | CAATCAGTGC | CCGTAAGTTT | CATTACTATT | TTCTATTATT | ATCTGCAACT | 720 |
| TTTTATTAGT | TAGGTTTTTT | TTGTTTGTTT | GTTTGTTTTC | AATTGATTAA | TTTACAAGAC | 780 |
| AAAGAACCTT | ATATTTCGTG | TTTTTCATTC | TAAAGGAAAA | AAAGCATAAA | GAAGATTCCA | 840 |
| CACACTTTAT | TGTGATAGTT | TTCAAAGTAA | AAAGTAATAG | ATTA | | 884 |

( 2 ) INFORMATION FOR SEQ ID NO:5:

( i ) SEQUENCE CHARACTERISTICS:
        ( A ) LENGTH: 1683
        ( B ) TYPE: nucleic acid
        ( C ) STRANDEDNESS: single
        ( D ) TOPOLOGY: linear ( i i ) MOLECULE TYPE: polypeptide ( x i ) SEQUENCE DESCRIPTION: SEQ ID NO:5:

| | | | | | | | | | | | | | | | | |
|---|---|---|---|---|---|---|---|---|---|---|---|---|---|---|---|---|
| TGA | GTA | CTC | CTG | CAA | ACT | ATA | CCC | GTG | TGC | CCC | TGT | GCG | AAC | CAG | AGG | 48 |
| Met | Ser | Thr | Pro | Ala | Asn | Tyr | Thr | Arg | Val | Pro | Leu | Cys | Glu | Pro | Glu | |
| | | | | 5 | | | | 10 | | | | | | 15 | | |
| AGC | TGC | CAG | ACG | ACA | TAC | AAA | AAG | AAA | ATG | AAT | ATG | GTA | CAC | TAG | ATT | 96 |
| Glu | Leu | Pro | Asp | Asp | Ile | Gln | Lys | Glu | Asn | Glu | Tyr | Gly | Thr | Leu | Asp | |
| | | | 20 | | | | 25 | | | | | 30 | | | | |
| CTC | CGG | GGC | ATT | TGT | ATC | AAG | TCA | AGT | CAC | GTC | ATG | GGA | AGC | CAC | TAC | 144 |
| Ser | Pro | Gly | His | Leu | Tyr | Gln | Val | Lys | Ser | Arg | His | Gly | Lys | Pro | Leu | |
| | | 35 | | | | 40 | | | | | 45 | | | | | |
| CTG | AGC | CCG | TTG | TCG | ACA | CCC | CTC | CTT | ATT | ACA | TTT | CTT | TGT | TAA | CAT | 192 |
| Pro | Glu | Pro | Val | Val | Asp | Thr | Pro | Pro | Tyr | Tyr | Ile | Ser | Leu | Leu | Thr | |
| | 50 | | | | | 55 | | | | | 60 | | | | | |
| ATC | TAA | ATT | ATT | TGA | TTC | TGA | TTA | TAT | TAG | GTC | ATG | TTC | ACG | ACT | TCT | 240 |
| Tyr | Leu | Asn | Try | Leu | Ile | Leu | Ile | Ile | Leu | Gly | His | Val | His | Asp | Phe | |
| 65 | | | | | 70 | | | | | 75 | | | | | 80 | |
| TAG | GTA | TGA | CCT | TCC | AAA | AAA | ACA | AAC | ATC | TGG | ATC | TTT | TAG | AGC | ATG | 288 |
| Leu | Gly | Met | Thr | Phe | Gln | Lys | Asn | Lys | His | Leu | Asp | Leu | Leu | Glu | His | |
| | | | | 85 | | | | 90 | | | | | 95 | | | |
| ATG | GGT | TAG | CAC | CTT | GGT | TTT | CAA | ATT | TCG | AGA | GTT | TTT | ATG | TCA | GGA | 336 |
| Asp | Gly | Leu | Ala | Pro | Trp | Phe | Ser | Asn | Phe | Glu | Ser | Phe | Tyr | Val | Arg | |
| | | | 100 | | | | 105 | | | | | 110 | | | | |
| GAA | TTA | AAA | TGA | GAA | TTG | ATG | ATT | GCT | TTT | CTA | GAC | CAA | CTA | CTG | GTG | 384 |
| Arg | Ile | Lys | Met | Arg | Ile | Asp | Asp | Cys | Phe | Ser | Arg | Pro | Thr | Thr | Gly | |
| | | 115 | | | | 120 | | | | | 125 | | | | | |
| TTC | CTG | GTA | GAT | TTA | TTC | GTT | GTA | TTG | ATA | GAA | TTT | CTC | ATA | ATA | TAA | 432 |
| Val | Pro | Gly | Arg | Phe | Ile | Arg | Cys | Ile | Asp | Arg | Ile | Ser | His | Asn | Ile | |
| | 130 | | | | | 135 | | | | | 140 | | | | | |
| ATG | AGT | ATT | TTA | CCT | ACT | CAG | GCG | CAG | TGT | ATC | CAT | GCA | TGA | ACT | TAT | 480 |
| Asn | Glu | Tyr | Phe | Thr | Tyr | Ser | Gly | Ala | Val | Tyr | Pro | Cys | Met | Asn | Leu | |
| 145 | | | | | 150 | | | | | 155 | | | | | 160 | |
| CAT | CAT | ATA | ACT | ATT | TAG | GCT | TCG | CAC | AAA | GTA | AGG | GTC | AAT | GTA | CCG | 528 |

```
       Ser  Ser  Tyr  Asn  Tyr  Leu  Gly  Phe  Ala  Gln  Ser  Lys  Gly  Gln  Cys  Thr
                           165                      170                      175

ATG  CCG  CCT  TGG  AAT  CTG  TCG  ATA  AAT  ATT  CTA  TTC  AAT  CTG  GTG  GTC             576
Asp  Ala  Ala  Leu  Glu  Ser  Val  Asp  Lys  Tyr  Ser  Ile  Gln  Ser  Gly  Gly
               180                      185                      190

CAA  GAG  CTC  AAA  TCG  GTA  CCA  CAG  ATT  TGC  ACA  TTA  AAG  CAG  AGA  AAT             624
Pro  Arg  Ala  Gln  Ile  Gly  Thr  Thr  Asp  Leu  His  Ile  Lys  Ala  Glu  Lys
          195                      200                      205

TAG  TTG  CTA  GAT  TTA  TCG  GTA  AGG  AGG  ATG  CCC  TCG  TTT  TTT  CGA  TGG             672
Leu  Val  Ala  Arg  Phe  Ile  Gly  Lys  Glu  Asp  Ala  Leu  Val  Phe  Ser  Met
     210                      215                      220

GTT  ATG  GTA  CAA  ATG  CAA  ACT  TGT  TCA  ACG  CTT  TCC  TCG  ATA  AAA  AGT             720
Gly  Tyr  Gly  Thr  Asn  Ala  Asn  Leu  Phe  Asn  Ala  Phe  Leu  Asp  Lys  Lys
225                      230                      235                      240

GTT  TAG  TTA  TCT  CTG  ACG  AAT  TGA  ACC  ACA  CCT  CTA  TTA  GAA  CAG  GTG             768
Cys  Leu  Val  Ile  Ser  Asp  Glu  Leu  Asn  His  Thr  Ser  Ile  Arg  Thr  Gly
               245                      250                      255

TTA  GGC  TTT  CTG  GTG  CTG  CTG  TGC  GAA  CTT  TCA  AGC  ATG  GTG  ATA  TGG             816
Val  Arg  Leu  Ser  Gly  Ala  Ala  Val  Arg  Thr  Phe  Lys  His  Gly  Asp  Met
          260                      265                      270

TGG  GTT  TAG  AAA  AGC  TTA  TCA  GAG  AAC  AGA  TAG  TAC  TTG  GTC  AAC  CAA             864
Val  Gly  Leu  Glu  Lys  Leu  Ile  Arg  Glu  Gln  Ile  Val  Leu  Gly  Gln  Pro
     275                      280                      285

AAA  CAA  ATC  GTC  CAT  GGA  AGA  AAA  TTT  TAA  TTT  GCG  CAG  AAG  GGT  TGT             912
Lys  Thr  Asn  Arg  Pro  Trp  Lys  Lys  Ile  Leu  Ile  Cys  Ala  Glu  Gly  Leu
290                      295                      300

TTT  CCA  TGG  AAG  GTA  CTT  TGT  GTA  ACT  TGC  CAA  AAT  TGG  TTG  AAT  TGA             960
Phe  Ser  Met  Glu  Gly  Thr  Leu  Cys  Asn  Leu  Pro  Lys  Leu  Val  Glu  Leu
305                      310                      315                      320

AGA  AGA  AAT  ATA  AAT  GTT  ACT  TGT  TTA  TCG  ATG  AAG  CCC  ATT  CTA  TAG            1008
Lys  Lys  Lys  Tyr  Lys  Cys  Tyr  Leu  Phe  Ile  Asp  Glu  Ala  His  Ser  Ile
               325                      330                      335

GCG  CTA  TGG  GCC  CAA  CTG  GTC  GCG  GTG  TTT  GTG  AAA  TAT  TTG  GCG  TTG            1056
Gly  Ala  Met  Gly  Pro  Thr  Gly  Arg  Gly  Val  Cys  Glu  Ile  Phe  Gly  Val
          340                      345                      350

ATC  CCA  AGG  ACG  TCG  ACA  TTC  TAA  TGG  GTA  CTT  TCA  CTA  AGT  CGT  TTG            1104
Asp  Pro  Lys  Asp  Val  Asp  Ile  Leu  Met  Gly  Thr  Phe  Thr  Lys  Ser  Phe
     355                      360                      365

GTG  CTG  CTG  GTG  GTT  ACA  TTG  CTG  CTG  ATC  AAT  GGA  TTA  TCG  ATA  GAC            1152
Gly  Ala  Ala  Gly  Gly  Tyr  Ile  Ala  Ala  Asp  Gln  Trp  Ile  Ile  Asp  Arg
370                      375                      380

TGA  GGT  TGG  ATT  TAA  CCA  CTG  TGA  GTT  ATA  GTG  AGT  CAA  TGC  CGG  CTC            1200
Leu  Arg  Leu  Asp  Leu  Thr  Thr  Val  Ser  Tyr  Ser  Glu  Ser  Met  Pro  Ala
385                      390                      395                      400

CTG  TTT  TAG  CTC  AAA  CTA  TTT  CCT  CAT  TAC  AAA  CCA  TTA  GTG  GTG  AAA            1248
Pro  Val  Leu  Ala  Gln  Thr  Ile  Ser  Ser  Leu  Gln  Thr  Ile  Ser  Gly  Glu
                    405                      410                      415

TAT  GTC  CCG  GAC  AAG  GTA  CTG  AAA  GAT  TGC  AAC  GTA  TAG  CCT  TTA  ATT            1296
Ile  Cys  Pro  Gly  Gln  Gly  Thr  Glu  Arg  Leu  Gln  Arg  Ile  Ala  Phe  Asn
               420                      425                      430

CCC  GTT  ATC  TAC  GTT  TAG  CTT  TGC  AAA  GGT  TAG  GAT  TTA  TTG  TCT  ACG            1344
Ser  Arg  Tyr  Leu  Arg  Leu  Ala  Leu  Gln  Arg  Leu  Gly  Phe  Ile  Val  Tyr
          435                      440                      445

GTG  TGG  CTG  ACT  CAC  CAG  TTA  TTC  CCT  TAC  TAC  TGT  ATT  GTC  CCT  CAA            1392
Glu  Val  Leu  Asp  Ser  Pro  Val  Ile  Pro  Leu  Leu  Leu  Tyr  Cys  Pro  Ser
     450                      455                      460

AGA  TGC  CCG  CAT  TTT  CGA  GAA  TGA  TGT  TAC  AAA  GAC  GGA  TTG  CTG  TTG            1440
Lys  Met  Pro  Ala  Phe  Ser  Arg  Met  Met  Leu  Gln  Arg  Arg  Ile  Ala  Val
465                      470                      475                      480

TTG  TTG  TTG  CTT  ATC  CTG  CTA  CTC  CGC  TGA  TCG  AAT  CAA  GAG  TAA  GAT            1488
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Val | Val | Val | Ala | Tyr<br>485 | Pro | Ala | Thr | Pro | Leu<br>490 | Ile | Glu | Ser | Arg | Val<br>495 | Arg | |
| TCT | GTA | TGT | CTG | CAT | CTT | TAA | CAA | AGG | AAG | ATA | TCG | ATT | ATT | TAC | TGC | 1536 |
| Phe | Cys | Met | Ser<br>500 | Ala | Ser | Leu | Thr | Lys<br>505 | Glu | Asp | Ile | Asp | Tyr<br>510 | Leu | Leu | |
| GTC | ATG | TTA | GTG | AAG | TTG | GTG | ACA | AAT | TGA | ATT | TGA | AAT | CAA | ATT | CCG | 1584 |
| Arg | His | Val<br>515 | Ser | Glu | Val | Gly | Asp<br>520 | Lys | Leu | Asn | Leu | Lys<br>525 | Ser | Asn | Ser | |
| GCA | AAT | CCA | GTT | ACG | ACG | GTA | AAC | GTC | AAA | GAT | GGG | ACA | TCG | AGG | AAG | 1632 |
| Gly | Lys<br>530 | Ser | Ser | Tyr | Asp | Gly<br>535 | Lys | Arg | Gln | Arg | Trp<br>540 | Asp | Ile | Glu | Glu | |
| TTA | TCA | GGA | GAA | CAC | CTG | AAG | ATT | GTA | AGG | ACG | ACA | AGT | ATT | TTG | TTA | 1680 |
| Val<br>545 | Ile | Arg | Arg | Thr | Pro<br>550 | Glu | Asp | Cys | Lys | Asp<br>555 | Asp | Lys | Tyr | Phe | Val<br>560 | |
| ATT<br>Asn | | | | | | | | | | | | | | | | 1683 |

( 2 ) INFORMATION FOR SEQ ID NO:6:

( i ) SEQUENCE CHARACTERISTICS:
        ( A ) LENGTH: 313
        ( B ) TYPE: nucleic acid
        ( C ) STRANDEDNESS: single
        ( D ) TOPOLOGY: linear ( i i ) MOLECULE TYPE: polynucleotide ( x i ) SEQUENCE DESCRIPTION: SEQ ID NO:6:

| | | | | | |
|---|---|---|---|---|---|
| GAATTTTACC | TAATTGCTAG | TTAGGTGAAA | AATTACAAAA | TTTCTGGAAG | ACGTTGGAAA | 60 |
| CACGCAACGT | CTTTTTGACA | TAAACTTAAA | ACTGCCAAAA | GTCAAACAAA | AATTGCAAAA | 120 |
| AAAGTAAAAA | AAGTTACGAA | AAAAAAAACA | TTTAAAAGAA | AGAAGAAGTT | AAAAGTGCAC | 180 |
| GCAATATGTT | CCAGGATATG | AAATGAAATA | CCTTTTGTTT | CACCTTTTAA | ATAATTTAAT | 240 |
| GTTATATATA | CAACTTTATC | GTATCATATT | CGCAATTACA | TTATACAAGA | ATGAGTTTTT | 300 |
| TTTCGCGACA | AAG | | | | | 313 |

( 2 ) INFORMATION FOR SEQ ID NO:7:

( i ) SEQUENCE CHARACTERISTICS:
        ( A ) LENGTH: 49
        ( B ) TYPE: amino acid
        ( C ) STRANDEDNESS: single
        ( D ) TOPOLOGY: linear ( i i ) MOLECULE TYPE: polypeptide ( x i ) SEQUENCE DESCRIPTION: SEQ ID NO:7:

|     |     |     |     |     |     |     |     |     |     |     |     |     |     |     |
| --- | --- | --- | --- | --- | --- | --- | --- | --- | --- | --- | --- | --- | --- | --- |
| Gln | Met | Val | Val | Thr<br>5 | Glu | Gly | Val | Phe | Ser<br>10 | Met | Asp | Gly | Asp | Ser<br>15 | Ala |
| Pro | Leu | Ala | Glu<br>20 | Ile | Gln | Gln | Val | Thr<br>25 | Gln | Gln | His | Asn | Gly<br>30 | Trp | Leu |
| Met | Val | Asp<br>35 | Asp | Ala | His | Gly | Thr<br>40 | Gly | Val | Ile | Gly | Glu<br>45 | Gln | Gly | Arg |
| Gly | | | | | | | | | | | | | | | |

( 2 ) INFORMATION FOR SEQ ID NO:8:

( i ) SEQUENCE CHARACTERISTICS:
        ( A ) LENGTH: 132
        ( B ) TYPE: amino acid
        ( C ) STRANDEDNESS: single
        ( D ) TOPOLOGY: linear (ii) MOLECULE TYPE: polypeptide (xi) SEQUENCE DESCRIPTION: SEQ ID NO:8:

| Phe | Ile | Cys | Gly | Thr | Gln | Asp | Ser | His | Lys | Glu | Leu | Glu | Gln | Lys | Leu |
|---|---|---|---|---|---|---|---|---|---|---|---|---|---|---|---|
| | | | | 5 | | | | | 10 | | | | | 15 | |

| Ala | Ala | Phe | Leu | Gly | Met | Glu | Asp | Ala | Ile | Leu | Tyr | Ser | Ser | Cys | Phe |
|---|---|---|---|---|---|---|---|---|---|---|---|---|---|---|---|
| | | | 20 | | | | | 25 | | | | | 30 | | |

| Asp | Ala | Asn | Gly | Gly | Leu | Phe | Glu | Thr | Leu | Leu | Gly | Xaa | Xaa | Ala | Glu |
| | | 35 | | | | | 40 | | | | | 45 | | | |

| Asp | Ala | Ile | Ile | Ser | Asp | Ala | Leu | Asn | His | Ala | Ser | Ile | Ile | Asp | Gly |
| | 50 | | | | | 55 | | | | | 60 | | | | |

| Val | Arg | Leu | Cys | Lys | Ala | Lys | Arg | Tyr | Arg | Tyr | Ala | Asn | Asn | Asp | Met |
| 65 | | | | | 70 | | | | 75 | | | | | | 80 |

| Gln | Glu | Leu | Glu | Ala | Arg | Leu | Lys | Glu | Ala | Arg | Glu | Arg | Glu | Xaa | Xaa |
| | | | | 85 | | | | | 90 | | | | | 95 | |

| Xaa | Xaa | Xaa | Xaa | Ala | Arg | His | Xaa | Val | Leu | Ile | Ala | Thr | Asp | Gly | Leu |
| | | | 100 | | | | | 105 | | | | | 110 | | |

| Phe | Ser | Met | Asp | Gly | Val | Ile | Ala | Asn | Leu | Lys | Gly | Val | Cys | Asp | Leu |
| | | | 115 | | | | 120 | | | | | 125 | | | |

| Ala | Asp | Lys | Tyr |
| | | | 130 |

(2) INFORMATION FOR SEQ ID NO:9:

(i) SEQUENCE CHARACTERISTICS:
  (A) LENGTH: 287
  (B) TYPE: amino acid
  (C) STRANDEDNESS: single
  (D) TOPOLOGY: linear (ii) MOLECULE TYPE: polypeptide (xi) SEQUENCE DESCRIPTION: SEQ ID NO:9:

| Leu | Ala | Ser | Asn | Asn | Phe | Leu | Gln | Leu | Ser | Ala | Thr | Glu | Pro | Val | Lys |
|---|---|---|---|---|---|---|---|---|---|---|---|---|---|---|---|
| | | | | 5 | | | | | 10 | | | | | 15 | |

| Glu | Val | Val | Lys | Thr | Thr | Ile | Lys | Asn | Tyr | Gly | Val | Gly | Ala | Cys | Gly |
| | | | 20 | | | | | 25 | | | | | 30 | | |

| Pro | Ala | Gly | Phe | Tyr | Gly | Asn | Gln | Asp | Val | His | Tyr | Thr | Leu | Glu | Tyr |
| | | 35 | | | | | 40 | | | | | 45 | | | |

| Asp | Leu | Ala | Gln | Phe | Phe | Gly | Thr | Gln | Gly | Ser | Val | Leu | Tyr | Gly | Gln |
| | 50 | | | | | 55 | | | | | 60 | | | | |

| Asp | Phe | Cys | Ala | Ala | Pro | Ser | Val | Leu | Pro | Ala | Phe | Thr | Lys | Xaa | Xaa |
| 65 | | | | | 70 | | | | | 75 | | | | | 80 |

| Arg | Gly | Asp | Val | Ile | Val | Ala | Asp | Asp | Gln | Val | Ser | Leu | Pro | Val | Gln |
| | | | | 85 | | | | | 90 | | | | | 95 | |

| Asn | Ala | Leu | Gln | Leu | Ser | Arg | Ser | Thr | Val | Tyr | Tyr | Phe | Asn | His | Asn |
| | | | 100 | | | | | 105 | | | | | 110 | | |

| Asp | Met | Asn | Ser | Leu | Glu | Cys | Leu | Leu | Asn | Glu | Leu | Thr | Glu | Gln | Glu |
| | | | 115 | | | | 120 | | | | | 125 | | | |

| Lys | Leu | Glu | Lys | Leu | Pro | Ala | Ile | Pro | Arg | Lys | Phe | Ile | Val | Thr | Glu |
| | | 130 | | | | | 135 | | | | | 140 | | | |

| Gly | Ile | Phe | His | Asn | Ser | Gly | Asp | Leu | Ala | Pro | Leu | Pro | Glu | Leu | Thr |
| 145 | | | | | 150 | | | | | 155 | | | | | 160 |

| Lys | Leu | Lys | Asn | Lys | Tyr | Lys | Phe | Arg | Leu | Phe | Val | Asp | Glu | Thr | Phe |
| | | | | 165 | | | | | 170 | | | | | 175 | |

| Ser | Ile | Gly | Val | Leu | Gly | Ala | Thr | Gly | Arg | Gly | Leu | Xaa | Xaa | Xaa | Xaa |
| | | | 180 | | | | | 185 | | | | | 190 | | |

```
Xaa Xaa Xaa Xaa Xaa Xaa Xaa Xaa Xaa Xaa Xaa Xaa Xaa Xaa Xaa Xaa
        195                 200                 205

Xaa Xaa Ser Glu His Xaa Xaa Phe Asn Met Asp Arg Ala Thr Ala Ile
    210                 215                 220

Asp Ile Thr Val Gly Ser Met Ala Thr Ala Leu Gly Ser Thr Gly Gly
225                 230                 235                 240

Phe Val Leu Gly Asp Ser Val Met Cys Leu His Gln Arg Ile Gly Ser
                245                 250                 255

Asn Ala Tyr Cys Phe Ser Ala Cys Leu Pro Ala Tyr Thr Val Thr Ser
            260                 265                 270

Val Ser Lys Val Leu Lys Leu Met Asp Ser Asn Asn Asp Ala Val
        275                 280                 285
```

( 2 ) INFORMATION FOR SEQ ID NO:10:

( i ) SEQUENCE CHARACTERISTICS:
        ( A ) LENGTH: 287
        ( B ) TYPE: amino acid
        ( C ) STRANDEDNESS: single
        ( D ) TOPOLOGY: linear ( i i ) MOLECULE TYPE: polypeptide ( x i ) SEQUENCE DESCRIPTION: SEQ ID NO:10:

```
Trp Cys Ser Asn Asp Tyr Leu Gly Ile Ser Arg His Pro Arg Val Leu
                5                   10                  15

Gln Ala Ile Glu Glu Thr Leu Lys Asn His Gly Ala Gly Ala Gly Gly
            20                  25                  30

Thr Arg Asn Ile Ser Gly Thr Ser Lys Phe His Val Glu Leu Glu Gln
        35                  40                  45

Glu Leu Ala Glu Leu His Gln Lys Asp Ser Ala Leu Leu Phe Ser Ser
50                  55                  60

Cys Phe Val Ala Asn Asp Ser Thr Leu Phe Thr Leu Ala Lys Leu Leu
65                  70                  75                  80

Pro Gly Cys Glu Ile Tyr Ser Asp Ala Gly Asn His Ala Ser Met Ile
                85                  90                  95

Gln Gly Ile Arg Asn Ser Gly Ala Ala Lys Phe Val Phe Arg His Asn
            100                 105                 110

Asp Pro Gly His Leu Lys Lys Leu Leu Xaa Xaa Xaa Xaa Xaa Xaa Xaa
        115                 120                 125

Xaa Xaa Glu Lys Ser Asp Pro Lys Thr Pro Lys Ile Val Ala Phe Glu
130                 135                 140

Thr Val His Ser Met Asp Gly Ala Ile Cys Pro Leu Glu Glu Leu Cys
145                 150                 155                 160

Asp Val Ala His Gln Tyr Gly Ala Leu Thr Phe Val Asp Glu Val His
                165                 170                 175

Ala Val Gly Leu Tyr Gly Ala Arg Gly Ala Gly Ile Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Gly Glu Arg Xaa Xaa Xaa Asp Gly Ile Met His Lys Leu
    210                 215                 220

Asp Ile Ile Ser Gly Thr Leu Gly Lys Ala Phe Gly Cys Val Gly Gly
225                 230                 235                 240

Tyr Ile Ala Ser Thr Arg Asp Leu Val Asp Met Val Arg Ser Tyr Ala
                245                 250                 255

Ala Gly Phe Ile Phe Thr Thr Ser Leu Pro Pro Met Met Leu Ser Gly
```

|     |     |     |     | 260 |     |     |     |     | 265 |     |     |     |     | 270 |
|---|---|---|---|---|---|---|---|---|---|---|---|---|---|---|

Ala Leu Glu Ser Val Arg Leu Leu Lys Gly Glu Glu Gly Gln Ala
            275                     280                 285

(2) INFORMATION FOR SEQ ID NO:11:

(i) SEQUENCE CHARACTERISTICS:
        (A) LENGTH: 287
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:11:

Trp Cys Ser Asn Asp Tyr Leu Gly Met Ser Arg His Pro Arg Val Cys
                  5                  10                  15

Gly Ala Val Met Asp Thr Lys Leu Gln His Gly Ala Gly Ala Gly Gly
            20                  25                  30

Thr Arg Asn Ile Ser Gly Thr Ser Lys Phe His Val Asp Leu Glu Lys
            35                  40                  45

Glu Leu Ala Asp Leu His Gly Lys Asp Ala Ala Leu Leu Phe Ser Ser
    50                  55                  60

Cys Phe Val Ala Asn Asp Ser Thr Leu Phe Thr Leu Ala Lys Met Leu
65                  70                  75                  80

Pro Gly Cys Gln Ile Tyr Ser Asp Ser Gly Asn His Ala Ser Met Ile
                85                  90                  95

Gln Gly Ile Arg Asn Ser Arg Val Pro Lys His Ile Phe Arg His Asn
            100                 105                 110

Asp Val Asn His Leu Arg Glu Leu Leu Xaa Xaa Xaa Xaa Xaa Xaa Xaa
            115                 120                 125

Xaa Xaa Lys Lys Ser Asp Pro Ser Thr Pro Lys Ile Val Ala Phe Glu
    130                 135                 140

Thr Val His Ser Met Asp Gly Ala Val Cys Pro Leu Glu Glu Leu Cys
145                 150                 155                 160

Asp Val Ala His Glu His Gly Ala Ile Thr Phe Val Asp Glu Val His
            165                 170                 175

Ala Val Gly Leu Tyr Gly Ala Arg Gly Gly Gly Ile Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
    195                 200                 205

Xaa Xaa Gly Asp Arg Xaa Xaa Xaa Xaa Asp Gly Val Met His Lys Met
    210                 215                 220

Asp Ile Ile Ser Gly Thr Leu Gly Lys Ala Phe Ala Cys Val Gly Gly
225                 230                 235                 240

Tyr Ile Ser Ser Thr Ser Ala Leu Ile Asp Thr Val Arg Ser Tyr Ala
                245                 250                 255

Ala Gly Phe Ile Phe Thr Thr Ser Leu Pro Pro Met Leu Leu Ala Gly
            260                 265                 270

Ala Leu Glu Ser Val Arg Thr Leu Lys Ser Ala Glu Gly Gln Val
            275                 280                 285

(2) INFORMATION FOR SEQ ID NO:12:

(i) SEQUENCE CHARACTERISTICS:
        (A) LENGTH: 287
        (B) TYPE: amino acid
        (C) STRANDEDNESS: single
        (D) TOPOLOGY: linear ( i i ) MOLECULE TYPE: polypeptide ( x i ) SEQUENCE DESCRIPTION: SEQ ID NO:12:

| Trp | Cys | Ser | Asn | Lys | Tyr | Leu | Ala | Leu | Ser | Lys | His | Pro | Glu | Val | Leu |
|---|---|---|---|---|---|---|---|---|---|---|---|---|---|---|---|
| | | | | 5 | | | | | 10 | | | | | 15 | |

| Asp | Ala | Met | His | Lys | Thr | Ile | Asp | Lys | Tyr | Gly | Cys | Gly | Ala | Gly | Gly |
|---|---|---|---|---|---|---|---|---|---|---|---|---|---|---|---|
| | | | 20 | | | | | 25 | | | | | 30 | | |

| Thr | Arg | Asn | Ile | Ala | Gly | His | Asn | Ile | Pro | Thr | Leu | Asn | Leu | Glu | Ala |
|---|---|---|---|---|---|---|---|---|---|---|---|---|---|---|---|
| | | 35 | | | | | 40 | | | | | 45 | | | |

| Glu | Leu | Ala | Thr | Leu | His | Lys | Lys | Glu | Gly | Ala | Leu | Val | Phe | Ser | Ser |
|---|---|---|---|---|---|---|---|---|---|---|---|---|---|---|---|
| | 50 | | | | | 55 | | | | | 60 | | | | |

| Cys | Tyr | Val | Ala | Asn | Asp | Ala | Val | Leu | Ser | Leu | Leu | Gly | Gln | Lys | Met |
|---|---|---|---|---|---|---|---|---|---|---|---|---|---|---|---|
| 65 | | | | | 70 | | | | | 75 | | | | | 80 |

| Lys | Asp | Leu | Val | Ile | Phe | Ser | Asp | Glu | Leu | Asn | His | Ala | Ser | Met | Ile |
|---|---|---|---|---|---|---|---|---|---|---|---|---|---|---|---|
| | | | | 85 | | | | | 90 | | | | | 95 | |

| Val | Gly | Ile | Lys | His | Ala | Asn | Val | Lys | Lys | His | Ile | Phe | Lys | His | Asn |
|---|---|---|---|---|---|---|---|---|---|---|---|---|---|---|---|
| | | | 100 | | | | | 105 | | | | | 110 | | |

| Asp | Leu | Asn | Glu | Leu | Glu | Gln | Leu | Leu | Xaa | Xaa | Xaa | Xaa | Xaa | Xaa | Xaa |
|---|---|---|---|---|---|---|---|---|---|---|---|---|---|---|---|
| | | 115 | | | | | 120 | | | | | 125 | | | |

| Xaa | Xaa | Gln | Ser | Tyr | Pro | Lys | Ser | Val | Pro | Lys | Leu | Ile | Ala | Phe | Glu |
|---|---|---|---|---|---|---|---|---|---|---|---|---|---|---|---|
| | 130 | | | | | 135 | | | | | 140 | | | | |

| Ser | Val | Tyr | Ser | Met | Ala | Gly | Ser | Val | Ala | Asp | Ile | Glu | Lys | Ile | Cys |
|---|---|---|---|---|---|---|---|---|---|---|---|---|---|---|---|
| 145 | | | | | 150 | | | | | 155 | | | | | 160 |

| Asp | Leu | Ala | Asp | Lys | Tyr | Gly | Ala | Leu | Thr | Phe | Leu | Asp | Glu | Val | His |
|---|---|---|---|---|---|---|---|---|---|---|---|---|---|---|---|
| | | | | 165 | | | | | 170 | | | | | 175 | |

| Ala | Val | Gly | Leu | Tyr | Gly | Pro | His | Gly | Ala | Gly | Val | Ala | Glu | His | Cys |
|---|---|---|---|---|---|---|---|---|---|---|---|---|---|---|---|
| | | | 180 | | | | | 185 | | | | | 190 | | |

| Asp | Phe | Glu | Ser | His | Arg | Ala | Ser | Gly | Ile | Ala | Thr | Pro | Lys | Thr | Asn |
|---|---|---|---|---|---|---|---|---|---|---|---|---|---|---|---|
| | | 195 | | | | | 200 | | | | | 205 | | | |

| Asp | Lys | Gly | Gly | Ala | Xaa | Xaa | Xaa | Xaa | Lys | Thr | Val | Met | Asp | Arg | Val |
|---|---|---|---|---|---|---|---|---|---|---|---|---|---|---|---|
| | 210 | | | | | 215 | | | | | 220 | | | | |

| Asp | Met | Ile | Thr | Gly | Thr | Leu | Gly | Lys | Ser | Phe | Gly | Ser | Val | Gly | Gly |
|---|---|---|---|---|---|---|---|---|---|---|---|---|---|---|---|
| 225 | | | | | 230 | | | | | 235 | | | | | 240 |

| Tyr | Gly | Ala | Ala | Ser | Arg | Lys | Leu | Ile | Asp | Trp | Phe | Arg | Ser | Phe | Ala |
|---|---|---|---|---|---|---|---|---|---|---|---|---|---|---|---|
| | | | | 245 | | | | | 250 | | | | | 255 | |

| Pro | Gly | Phe | Ile | Phe | Thr | Thr | Thr | Leu | Pro | Pro | Ser | Val | Met | Ala | Gly |
|---|---|---|---|---|---|---|---|---|---|---|---|---|---|---|---|
| | | | 260 | | | | | 265 | | | | | 270 | | |

| Ala | Thr | Ala | Ala | Ile | Arg | Tyr | Gln | Arg | Cys | His | Ile | Asp | Leu | Arg | |
|---|---|---|---|---|---|---|---|---|---|---|---|---|---|---|---|
| | | 275 | | | | | 280 | | | | | 285 | | | |

( 2 ) INFORMATION FOR SEQ ID NO:13:

( i ) SEQUENCE CHARACTERISTICS:
        ( A ) LENGTH: 625
        ( B ) TYPE: amino acid
        ( C ) STRANDEDNESS: single
        ( D ) TOPOLOGY: linear ( i i ) MOLECULE TYPE: polypeptide ( x i ) SEQUENCE DESCRIPTION: SEQ ID NO:13:

| Met | Ala | His | Ile | Pro | Glu | Xaa | Xaa | Xaa | Xaa | Val | Leu | Pro | Lys | Ser | Ile |
|---|---|---|---|---|---|---|---|---|---|---|---|---|---|---|---|
| | | | | 5 | | | | | 10 | | | | | 15 | |

| Pro | Ile | Pro | Ala | Phe | Ile | Val | Thr | Thr | Ser | Ser | Tyr | Leu | Trp | Tyr | Tyr |
|---|---|---|---|---|---|---|---|---|---|---|---|---|---|---|---|
| | | | 20 | | | | | 25 | | | | | 30 | | |

| Phe | Asn | Leu | Val | Leu | Thr | Gln | Ile | Pro | Gly | Gly | Gln | Phe | Ile | Val | Ser |
|---|---|---|---|---|---|---|---|---|---|---|---|---|---|---|---|
| | | 35 | | | | | 40 | | | | | 45 | | | |

```
Tyr  Ile  Lys  Lys  Ser  His  His  Asp  Asp  Pro  Tyr  Arg  Thr  Thr  Val  Glu
     50             55                       60

Xaa  Xaa  Xaa  Xaa  Xaa  Ile  Gly  Leu  Ile  Leu  Tyr  Gly  Xaa  Xaa  Xaa
65             70                       75                            80

Ile  Ile  Tyr  Tyr  Leu  Ser  Lys  Pro  Gln  Gln  Lys  Lys  Ser  Leu  Gln  Ala
               85                       90                       95

Gln  Lys  Pro  Asn  Xaa  Xaa  Xaa  Xaa  Leu  Ser  Pro  Gln  Glu  Ile  Asp  Ala
          100                      105                      110

Leu  Ile  Glu  Asp  Trp  Glu  Pro  Glu  Pro  Leu  Val  Asp  Pro  Ser  Ala  Thr
          115                      120                      125

Asp  Glu  Gln  Ser  Trp  Arg  Val  Ala  Lys  Thr  Pro  Val  Thr  Met  Glu  Met
     130                      135                 140

Pro  Ile  Xaa  Gln  Asn  His  Ile  Thr  Ile  Thr  Arg  Asn  Asn  Leu  Gln  Glu
145                      150                      155                      160

Lys  Tyr  Thr  Xaa  Xaa  Xaa  Asn  Val  Phe  Xaa  Xaa  Xaa  Asn  Leu  Ala  Ser
               165                      170                      175

Asn  Asn  Phe  Leu  Gln  Leu  Ser  Ala  Thr  Glu  Xaa  Pro  Val  Lys  Glu  Val
               180                      185                 190

Val  Lys  Thr  Thr  Ile  Lys  Asn  Tyr  Gly  Val  Gly  Ala  Cys  Gly  Pro  Ala
          195                      200                 205

Gly  Phe  Tyr  Gly  Asn  Gln  Asp  Val  His  Tyr  Thr  Leu  Glu  Tyr  Asp  Leu
     210                      215                 220

Ala  Gln  Phe  Phe  Gly  Thr  Gln  Gly  Ser  Val  Leu  Tyr  Gly  Gln  Asp  Phe
225                      230                 235                           240

Cys  Ala  Ala  Pro  Ser  Val  Leu  Pro  Ala  Phe  Thr  Lys  Arg  Xaa  Gly  Asp
               245                      250                 255

Val  Ile  Val  Xaa  Ala  Asp  Asp  Gln  Val  Ser  Leu  Pro  Val  Gln  Asn  Ala
          260                      265                      270

Leu  Gln  Leu  Ser  Arg  Ser  Thr  Val  Tyr  Tyr  Phe  Asn  His  Asn  Asp  Met
          275                      280                      285

Asn  Ser  Leu  Glu  Cys  Leu  Leu  Asn  Glu  Leu  Thr  Glu  Gln  Glu  Lys  Leu
     290                      295                      300

Glu  Lys  Leu  Pro  Ala  Ile  Pro  Arg  Lys  Phe  Ile  Val  Thr  Glu  Gly  Ile
305                      310                      315                      320

Phe  His  Asn  Ser  Gly  Asp  Leu  Ala  Pro  Leu  Pro  Glu  Leu  Thr  Lys  Leu
               325                      330                      335

Lys  Asn  Lys  Tyr  Lys  Phe  Arg  Leu  Phe  Val  Asp  Glu  Thr  Phe  Ser  Ile
               340                      345                 350

Gly  Val  Leu  Gly  Ala  Thr  Gly  Arg  Gly  Leu  Ser  Glu  His  Xaa  Xaa  Phe
          355                      360                      365

Asn  Met  Asp  Arg  Ala  Thr  Ala  Ile  Xaa  Xaa  Xaa  Xaa  Xaa  Xaa  Xaa  Xaa
     370                      375                      380

Xaa  Xaa  Xaa  Xaa  Xaa  Xaa  Xaa  Xaa  Xaa  Asp  Ile  Thr  Val  Gly  Ser
385                      390                      395                      400

Met  Ala  Thr  Ala  Leu  Gly  Ser  Thr  Gly  Gly  Phe  Val  Leu  Gly  Asp  Ser
               405                      410                      415

Val  Met  Cys  Leu  His  Gln  Arg  Ile  Gly  Ser  Asn  Ala  Tyr  Cys  Phe  Ser
               420                      425                 430

Ala  Cys  Leu  Pro  Ala  Tyr  Thr  Val  Thr  Ser  Val  Ser  Lys  Val  Leu  Lys
               435                 440                      445

Leu  Met  Asp  Ser  Asn  Asn  Asp  Ala  Val  Gln  Thr  Leu  Gln  Lys  Leu  Ser
     450                      455                      460

Lys  Xaa  Ser  Leu  His  Asp  Ser  Phe  Ala  Ser  Asp  Asp  Ser  Leu  Arg  Ser
```

```
                    465                      470                      475                      480
Tyr  Val  Ile  Val  Thr  Ser  Ser  Pro  Val  Ser  Pro  Val  Leu  His  Leu  Gln
                    485                      490                      495

Leu  Thr  Pro  Ala  Tyr  Arg  Ser  Arg  Lys  Phe  Gly  Xaa  Xaa  Xaa  Xaa  Xaa
               500                      505                      510

Xaa  Xaa  Xaa  Xaa  Tyr  Thr  Cys  Glu  Gln  Leu  Phe  Glu  Thr  Met  Ser  Ala
               515                      520                      525

Leu  Gln  Lys  Lys  Ser  Gln  Thr  Asn  Lys  Phe  Ile  Glu  Pro  Tyr  Glu  Glu
          530                      535                      540

Glu  Glu  Lys  Phe  Leu  Gln  Ser  Ile  Val  Asp  His  Ala  Leu  Ile  Asn  Tyr
545                      550                      555                           560

Asn  Val  Leu  Ile  Thr  Arg  Asn  Xaa  Xaa  Xaa  Xaa  Thr  Ile  Val  Leu  Lys
                    565                      570                      575

Gln  Glu  Thr  Leu  Pro  Ile  Val  Pro  Ser  Leu  Lys  Ile  Cys  Cys  Asn  Ala
               580                      585                      590

Ala  Met  Ser  Pro  Glu  Glu  Leu  Lys  Asn  Ala  Xaa  Xaa  Xaa  Cys  Glu  Ser
          595                      600                      605

Val  Lys  Gln  Ser  Ile  Leu  Ala  Cys  Cys  Gln  Glu  Ser  Asn  Xaa  Xaa  Xaa
     610                      615                      620

Lys
625

( 2 ) INFORMATION FOR SEQ ID NO:14:

( i ) SEQUENCE CHARACTERISTICS:
               ( A ) LENGTH: 625
               ( B ) TYPE: amino acid
               ( C ) STRANDEDNESS: single
               ( D ) TOPOLOGY: linear ( i i ) MOLECULE TYPE: polypeptide ( x i ) SEQUENCE DESCRIPTION: SEQ ID NO:14:

Met  Ser  Thr  Pro  Ala  Asn  Tyr  Thr  Arg  Val  Pro  Leu  Cys  Glu  Pro  Glu
               5                        10                       15

Glu  Leu  Pro  Asp  Asp  Ile  Gln  Lys  Glu  Asn  Glu  Tyr  Xaa  Xaa  Xaa  Xaa
               20                       25                       30

Xaa  Xaa  Xaa  Gly  Thr  Leu  Asp  Ser  Pro  Gly  His  Leu  Tyr  Gln  Val  Xaa
          35                       40                       45

Xaa  Xaa  Xaa  Lys  Ser  Arg  His  Gly  Lys  Pro  Leu  Pro  Glu  Pro  Val  Val
     50                       55                       60

Asp  Thr  Pro  Pro  Tyr  Tyr  Ile  Ser  Leu  Leu  Thr  Tyr  Leu  Asn  Tyr  Leu
65                       70                       75                            80

Ile  Leu  Ile  Ile  Leu  Gly  His  Val  His  Asp  Phe  Leu  Gly  Met  Thr  Phe
                    85                       90                       95

Gln  Lys  Asn  Lys  His  Leu  Asp  Leu  Leu  Glu  His  Asp  Gly  Leu  Ala  Pro
               100                      105                      110

Trp  Phe  Ser  Asn  Phe  Glu  Ser  Phe  Tyr  Val  Arg  Arg  Ile  Lys  Met  Arg
               115                      120                      125

Ile  Asp  Asp  Cys  Phe  Xaa  Xaa  Ser  Arg  Pro  Thr  Thr  Gly  Val  Pro  Gly
     130                      135                      140

Arg  Phe  Xaa  Ile  Arg  Cys  Ile  Asp  Arg  Ile  Ser  His  Asn  Ile  Asn  Glu
145                      150                      155                           160

Tyr  Phe  Thr  Tyr  Ser  Gly  Ala  Val  Tyr  Pro  Cys  Met  Asn  Leu  Ser  Ser
                    165                      170                      175

Tyr  Asn  Tyr  Leu  Gly  Phe  Ala  Gln  Ser  Lys  Gly  Gln  Cys  Thr  Asp  Ala
               180                      185                      190
```

```
Ala Leu Glu Ser Val Asp Lys Tyr Ser Ile Gln Ser Gly Gly Pro Arg
        195                 200                 205

Ala Gln Ile Gly Thr Thr Asp Leu His Ile Lys Ala Glu Lys Leu Val
    210                 215                 220

Ala Arg Phe Ile Gly Lys Glu Asp Ala Leu Val Phe Ser Met Gly Tyr
225                 230                 235                 240

Gly Thr Asn Ala Asn Leu Phe Asn Ala Phe Leu Asp Lys Xaa Lys Cys
                245                 250                 255

Leu Val Ile Xaa Ser Asp Glu Leu Asn His Thr Ser Ile Arg Thr Gly
            260                 265                 270

Val Arg Leu Ser Gly Ala Ala Val Arg Thr Phe Lys His Gly Asp Met
        275                 280                 285

Val Gly Leu Glu Lys Leu Ile Arg Glu Gln Ile Val Leu Gly Gln Pro
    290                 295                 300

Lys Thr Asn Arg Pro Trp Lys Lys Ile Leu Ile Cys Ala Glu Gly Leu
305                 310                 315                 320

Phe Ser Met Glu Gly Thr Leu Cys Asn Leu Pro Lys Leu Val Glu Leu
                325                 330                 335

Lys Lys Lys Tyr Lys Cys Tyr Leu Phe Ile Asp Glu Ala His Ser Ile
            340                 345                 350

Gly Ala Met Gly Pro Thr Gly Arg Gly Val Cys Glu Ile Xaa Xaa Phe
        355                 360                 365

Gly Val Asp Xaa Pro Lys Asp Val Xaa Xaa Xaa Xaa Xaa Xaa Xaa Xaa
    370                 375                 380

Xaa Xaa Xaa Xaa Xaa Xaa Xaa Xaa Xaa Asp Ile Leu Met Gly Thr
385                 390                 395                 400

Phe Thr Lys Ser Phe Gly Ala Ala Gly Gly Tyr Ile Ala Ala Asp Gln
                405                 410                 415

Trp Ile Ile Asp Arg Leu Arg Leu Asp Leu Thr Thr Val Ser Tyr Ser
            420                 425                 430

Glu Ser Met Pro Ala Pro Val Leu Ala Gln Thr Ile Ser Ser Leu Gln
        435                 440                 445

Thr Ile Ser Gly Glu Ile Cys Pro Gly Gln Gly Thr Glu Arg Leu Gln
    450                 455                 460

Arg Ile Ala Phe Asn Ser Arg Tyr Leu Arg Leu Ala Leu Gln Arg Leu
465                 470                 475                 480

Gly Phe Ile Val Tyr Glu Val Ala Asp Ser Pro Val Ile Pro Leu Leu
                485                 490                 495

Leu Xaa Xaa Xaa Tyr Cys Pro Ser Lys Met Xaa Xaa Xaa Xaa Xaa
            500                 505                 510

Xaa Xaa Xaa Xaa Xaa Xaa Xaa Xaa Pro Ala Phe Ser Arg Met Xaa Met
        515                 520                 525

Leu Gln Arg Arg Ile Ala Val Xaa Xaa Val Val Val Ala Tyr Pro Ala
530                 535                 540

Thr Pro Xaa Leu Ile Glu Ser Arg Val Arg Phe Cys Met Ser Ala Xaa
545                 550                 555                 560

Xaa Ser Leu Thr Lys Glu Asp Xaa Xaa Xaa Xaa Ile Asp Tyr Leu Leu
                565                 570                 575

Arg His Val Ser Glu Val Gly Asp Lys Leu Asn Leu Lys Ser Asn Ser
            580                 585                 590

Gly Lys Ser Ser Tyr Asp Gly Lys Arg Gln Arg Trp Asp Ile Glu Glu
        595                 600                 605

Val Ile Arg Arg Thr Pro Glu Asp Cys Lys Asp Asp Lys Tyr Phe Val
```

|     |     |     | 610 |     |     |     |     | 615 |     |     |     |     | 620 |     |
| --- | --- | --- | --- | --- | --- | --- | --- | --- | --- | --- | --- | --- | --- | --- |

Asn
625

(2) INFORMATION FOR SEQ ID NO:15:

(i) SEQUENCE CHARACTERISTICS:
        (A) LENGTH: 625
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:15:

| Met | Gln | Arg | Xaa | Ser | Ile | Phe | Ala | Arg | Xaa | Xaa | Phe | Gly | Asn | Ser | Ser |
| --- | --- | --- | --- | --- | --- | --- | --- | --- | --- | --- | --- | --- | --- | --- | --- |
|     |     |     | 5   |     |     |     |     |     | 10  |     |     |     |     | 15  |     |
| Ala | Ala | Val | Ser | Thr | Leu | Asn | Arg | Xaa | Xaa | Xaa | Xaa | Xaa | Xaa | Xaa | Xaa |
|     |     |     | 20  |     |     |     |     | 25  |     |     |     |     | 30  |     |     |
| Xaa | Xaa | Xaa | Xaa | Leu | Ser | Thr | Thr | Ala | Ala | Pro | His | Ala | Lys | Asn | Gly |
|     |     |     | 35  |     |     |     | 40  |     |     |     |     | 45  |     |     |     |
| Tyr | Ala | Thr | Ala | Thr | Gly | Ala | Gly | Ala | Ala | Ala | Ala | Thr | Ala | Thr | Ala |
|     | 50  |     |     |     |     | 55  |     |     |     |     |     | 60  |     |     |     |
| Ser | Ser | Xaa | Xaa | Xaa | Xaa | Xaa | Xaa | Xaa | Xaa | Xaa | Xaa | Xaa | Xaa | Xaa | Xaa |
| 65  |     |     |     |     | 70  |     |     |     |     |     | 75  |     |     |     | 80  |
| Xaa | Xaa | Xaa | Xaa | Xaa | Thr | His | Ala | Ala | Ala | Ala | Ala | Ala | Ala | Ala | Ala |
|     |     |     |     | 85  |     |     |     |     | 90  |     |     |     |     | 95  |     |
| Asn | His | Ser | Thr | Gln | Glu | Ser | Gly | Phe | Asp | Tyr | Glu | Gly | Leu | Ile | Asp |
|     |     |     | 100 |     |     |     |     | 105 |     |     |     |     | 110 |     |     |
| Xaa | Xaa | Ser | Glu | Leu | Gln | Xaa | Xaa | Xaa | Xaa | Xaa | Xaa | Xaa | Lys | Lys | Arg |
|     |     |     | 115 |     |     |     |     | 120 |     |     |     |     | 125 |     |     |
| Leu | Asp | Lys | Ser | Tyr | Arg | Tyr | Phe | Asn | Asn | Ile | Asn | Arg | Leu | Ala | Lys |
|     | 130 |     |     |     |     | 135 |     |     |     |     | 140 |     |     |     |     |
| Glu | Phe | Pro | Leu | Ala | His | Arg | Gln | Arg | Glu | Ala | Asp | Lys | Val | Thr | Val |
| 145 |     |     |     |     | 150 |     |     |     |     | 155 |     |     |     |     | 160 |
| Trp | Xaa | Xaa | Xaa | Xaa | Xaa | Xaa | Xaa | Xaa | Xaa | Cys | Xaa | Xaa | Xaa | Xaa | Ser |
|     |     |     |     | 165 |     |     |     |     |     | 170 |     |     |     | 175 |     |
| Asn | Asp | Tyr | Leu | Ala | Leu | Ser | Lys | Xaa | His | Pro | Gln | Val | Leu | Asp | Ala |
|     |     |     | 180 |     |     |     |     | 185 |     |     |     |     | 190 |     |     |
| Met | His | Lys | Thr | Ile | Asp | Lys | Tyr | Gly | Cys | Gly | Ala | Gly | Gly | Thr | Arg |
|     |     | 195 |     |     |     |     |     | 200 |     |     |     |     | 205 |     |     |
| Asn | Ile | Ala | Gly | His | Asn | Ile | Pro | Thr | Leu | Asn | Leu | Glu | Ala | Glu | Leu |
|     | 210 |     |     |     |     | 215 |     |     |     |     | 220 |     |     |     |     |
| Ala | Thr | Leu | His | Lys | Lys | Glu | Gly | Ala | Leu | Val | Phe | Ser | Ser | Cys | Tyr |
| 225 |     |     |     |     | 230 |     |     |     |     | 235 |     |     |     |     | 240 |
| Val | Ala | Asn | Asp | Ala | Val | Leu | Ser | Leu | Leu | Gly | Gln | Lys | Met | Lys | Asp |
|     |     |     |     | 245 |     |     |     |     | 250 |     |     |     |     | 255 |     |
| Leu | Val | Ile | Phe | Ser | Asp | Glu | Leu | Asn | His | Ala | Ser | Met | Ile | Val | Gly |
|     |     |     | 260 |     |     |     |     |     | 265 |     |     |     | 270 |     |     |
| Ile | Lys | His | Ala | Asn | Val | Lys | Lys | His | Ile | Phe | Lys | His | Asn | Asp | Leu |
|     |     | 275 |     |     |     |     | 280 |     |     |     |     | 285 |     |     |     |
| Asn | Glu | Leu | Glu | Gln | Leu | Leu | Xaa | Xaa | Xaa | Xaa | Xaa | Xaa | Xaa | Xaa | Xaa |
|     | 290 |     |     |     |     | 295 |     |     |     |     | 300 |     |     |     |     |
| Gln | Ser | Tyr | Pro | Lys | Ser | Val | Pro | Lys | Leu | Ile | Ala | Phe | Glu | Ser | Val |
| 305 |     |     |     |     | 310 |     |     |     |     | 315 |     |     |     |     | 320 |
| Tyr | Ser | Met | Ala | Gly | Ser | Val | Ala | Asp | Ile | Glu | Lys | Ile | Cys | Asp | Leu |
|     |     |     |     | 325 |     |     |     |     | 330 |     |     |     |     | 335 |     |

| | | | | | | | | | | | | | | |
|---|---|---|---|---|---|---|---|---|---|---|---|---|---|---|
| Ala | Asp | Lys | Tyr 340 | Gly | Ala | Leu | Thr 345 | Phe | Leu | Asp | Glu | Val | His 350 | Ala | Val |
| Gly | Leu | Tyr 355 | Gly | Pro | His | Gly | Ala 360 | Gly | Val | Ala | Glu | His 365 | Cys | Asp | Phe |
| Glu | Ser 370 | His | Arg | Ala | Ser | Gly 375 | Ile | Ala | Thr | Pro | Lys 380 | Thr | Asn | Asp | Lys |
| Gly 385 | Gly | Ala | Lys | Thr | Val 390 | Met | Asp | Arg | Val | Asp 395 | Met | Ile | Thr | Gly | Thr 400 |
| Leu | Gly | Lys | Ser | Phe 405 | Gly | Ser | Val | Gly | Gly 410 | Tyr | Val | Ala | Ala | Ser 415 | Arg |
| Lys | Leu | Ile | Asp 420 | Trp | Phe | Arg | Ser | Phe 425 | Ala | Pro | Gly | Phe | Ile 430 | Phe | Thr |
| Thr | Thr | Leu 435 | Pro | Pro | Ser | Val | Met 440 | Ala | Gly | Ala | Thr | Ala 445 | Ala | Ile | Arg |
| Tyr | Gln 450 | Arg | Cys | His | Ile | Asp 455 | Leu | Arg | Thr | Ser | Gln 460 | Gln | Lys | Xaa | Xaa |
| Xaa 465 | Xaa | Xaa | Xaa | His | Thr 470 | Met | Tyr | Val | Lys | Lys 475 | Ala | Phe | His | Glu | Leu 480 |
| Gly | Ile | Pro | Val | Ile 485 | Pro | Asn | Pro | Xaa | Ser 490 | His | Ile | Val | Pro | Val 495 | Leu |
| Ile | Gly | Asn | Ala 500 | Asp | Leu | Ala | Lys | Gln 505 | Ala | Ser | Asp | Ile | Leu 510 | Ile | Asn |
| Lys | His | Gln 515 | Ile | Tyr | Val | Gln | Ala 520 | Ile | Asn | Phe | Pro | Thr 525 | Val | Ala | Arg |
| Gly | Thr 530 | Glu | Arg | Leu | Arg | Ile 535 | Thr | Pro | Thr | Pro | Gly 540 | His | Thr | Asn | Asp |
| Leu 545 | Ser | Asp | Ile | Leu | Ile 550 | Asn | Ala | Val | Asp | Asp 555 | Val | Phe | Asn | Glu | Leu 560 |
| Gln | Leu | Pro | Arg | Val 565 | Arg | Asp | Trp | Glu | Ser 570 | Gln | Gly | Gly | Leu | Leu 575 | Gly |
| Val | Gly | Glu | Ser 580 | Gly | Phe | Val | Glu | Glu 585 | Ser | Asn | Leu | Trp | Thr 590 | Ser | Ser |
| Gln | Leu | Ser 595 | Leu | Thr | Asn | Asp | Asp 600 | Leu | Asn | Pro | Xaa | Xaa 605 | Xaa | Xaa | Asn |
| Val | Arg 610 | Asp | Pro | Ile | Val | Lys 615 | Gln | Leu | Glu | Val | Ser 620 | Ser | Gly | Ile | Lys |
| Gln 625 | | | | | | | | | | | | | | | |